US006341400B1

(12) United States Patent
Kobayashi et al.

(10) Patent No.: US 6,341,400 B1
(45) Date of Patent: Jan. 29, 2002

(54) TOOTHBRUSH

(75) Inventors: Kiyoshi Kobayashi; Yukito Kouno; Norihiro Hukuba; Hiroshi Hukuba, all of Nagareyama (JP)

(73) Assignee: Hukuba Dental Corp. (JP)

( * ) Notice: Subject to any disclaimer, the term of this patent is extended or adjusted under 35 U.S.C. 154(b) by 0 days.

(21) Appl. No.: 09/463,398

(22) PCT Filed: May 31, 1999

(86) PCT No.: PCT/JP99/02898

§ 371 Date: May 19, 2000

§ 102(e) Date: May 19, 2000

(87) PCT Pub. No.: WO99/62372

PCT Pub. Date: Dec. 9, 1999

(30) Foreign Application Priority Data

May 29, 1998 (JP) .......................................... 10-149135

(51) Int. Cl.[7] .................................................. A46B 9/04
(52) U.S. Cl. ........................................ 15/105; 15/167.1
(58) Field of Search ................................ 15/105, 167.1; 604/20

(56) References Cited

U.S. PATENT DOCUMENTS

| | | | | |
|---|---|---|---|---|
| 4,502,497 A | * | 3/1985 | Siahou | |
| 4,691,718 A | * | 9/1987 | Sakuma et al. | |
| 4,726,806 A | * | 2/1988 | Hukuba | |
| 4,944,296 A | * | 7/1990 | Suyama | |
| 4,969,868 A | * | 11/1990 | Wang | |
| 5,133,102 A | * | 7/1992 | Sakuma | |
| 5,372,501 A | * | 12/1994 | Shalvi | |
| 5,921,251 A | * | 7/1999 | Joshi | |

FOREIGN PATENT DOCUMENTS

| | | | | |
|---|---|---|---|---|
| GB | 2317555 A | * | 4/1998 | |
| JP | 53-64655 | | 6/1978 | |
| JP | 60-45362 | | 3/1985 | |
| JP | 2-224615 | | 9/1990 | |
| JP | 2-283311 | | 11/1990 | |
| JP | 2-309908 | | 12/1990 | |
| JP | 8-10046 | | 1/1996 | |
| JP | 8-80219 A | * | 3/1996 | |
| JP | 9-65931 A | * | 3/1997 | |
| JP | 9-103326 A | * | 4/1997 | |
| JP | 10-192055 A | * | 7/1998 | |

* cited by examiner

Primary Examiner—Terrence R. Till
(74) Attorney, Agent, or Firm—Nixon Peabody LLP; Thomas W. Cole

(57) ABSTRACT

An ion toothbrush which can be tested on the supply voltage by turning on a switch, and concerning which assembling steps are simplified. This ion toothbrush comprises: a head (50) with brush bristles (51) implanted therein; a handle (10); and a battery (14) received in the handle (10). One electrode of the battery (14) is conductively connected with the external surface of the handle (10), and the other electrode is conductively connected with the vicinity of the implanted area of the brush bristles (51) at the head (50). This ion toothbrush further comprises: an LED (18) with its one terminal (18B) connected to one electrode of the battery (14), and with the other terminal (18A) connected to the other electrode of the battery; a spindle capable-of conductively connecting the other electrode of the battery. (14) with the vicinity of the implanted area and also capable of conductively connecting with the terminal (18A); and a switch (22) for opening or closing an electric circuit containing the LED (18), the spindle (26), and the battery (14).

21 Claims, 23 Drawing Sheets

FIG.2
FIG.1
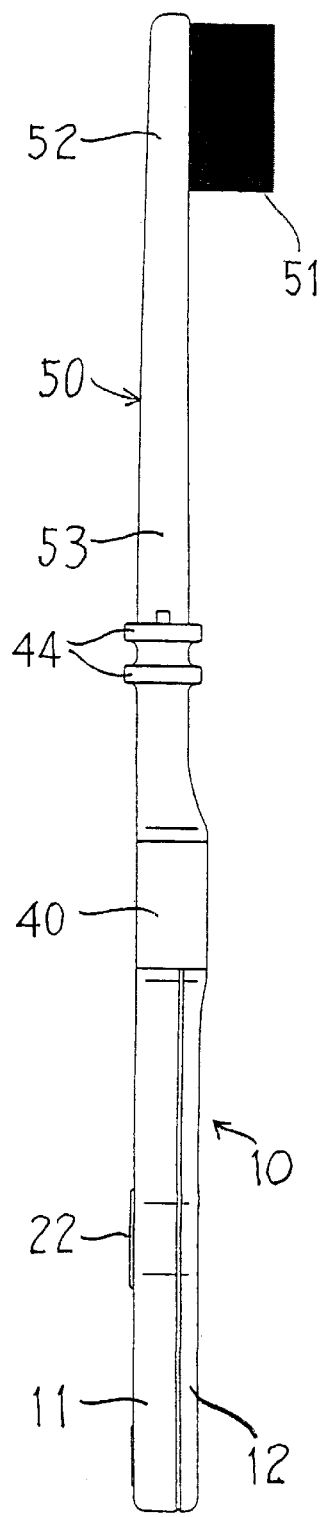
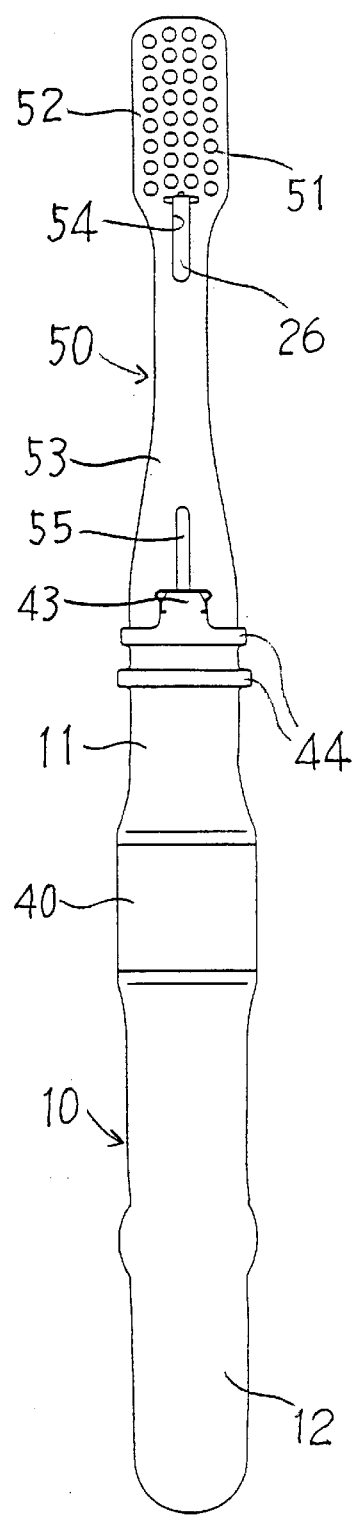

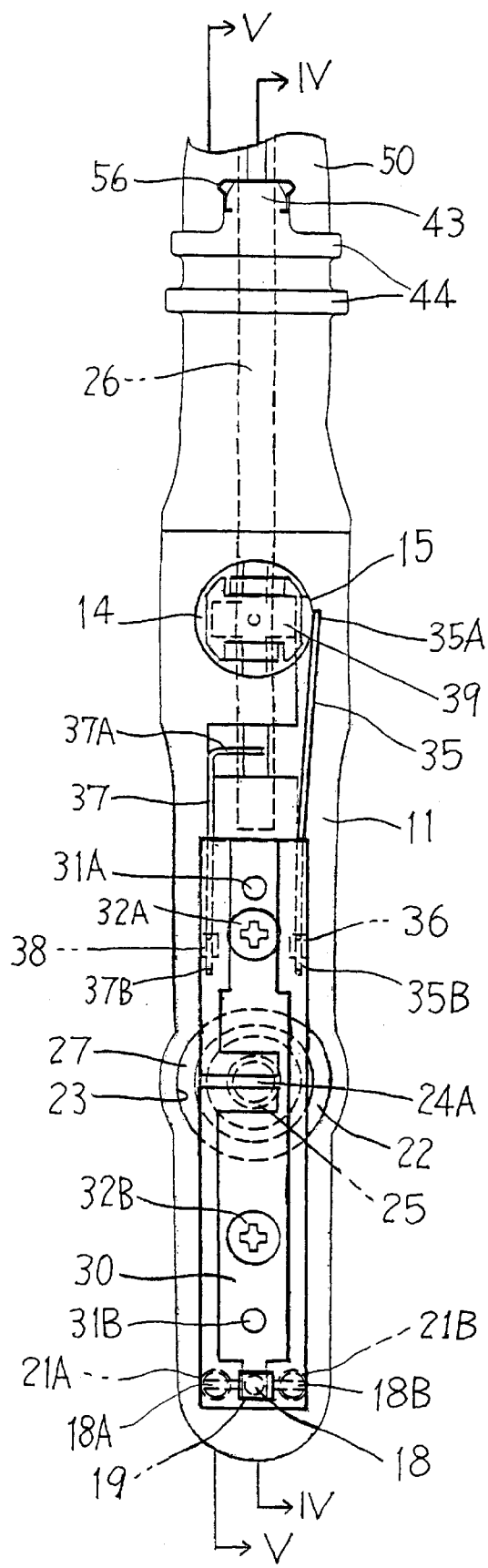

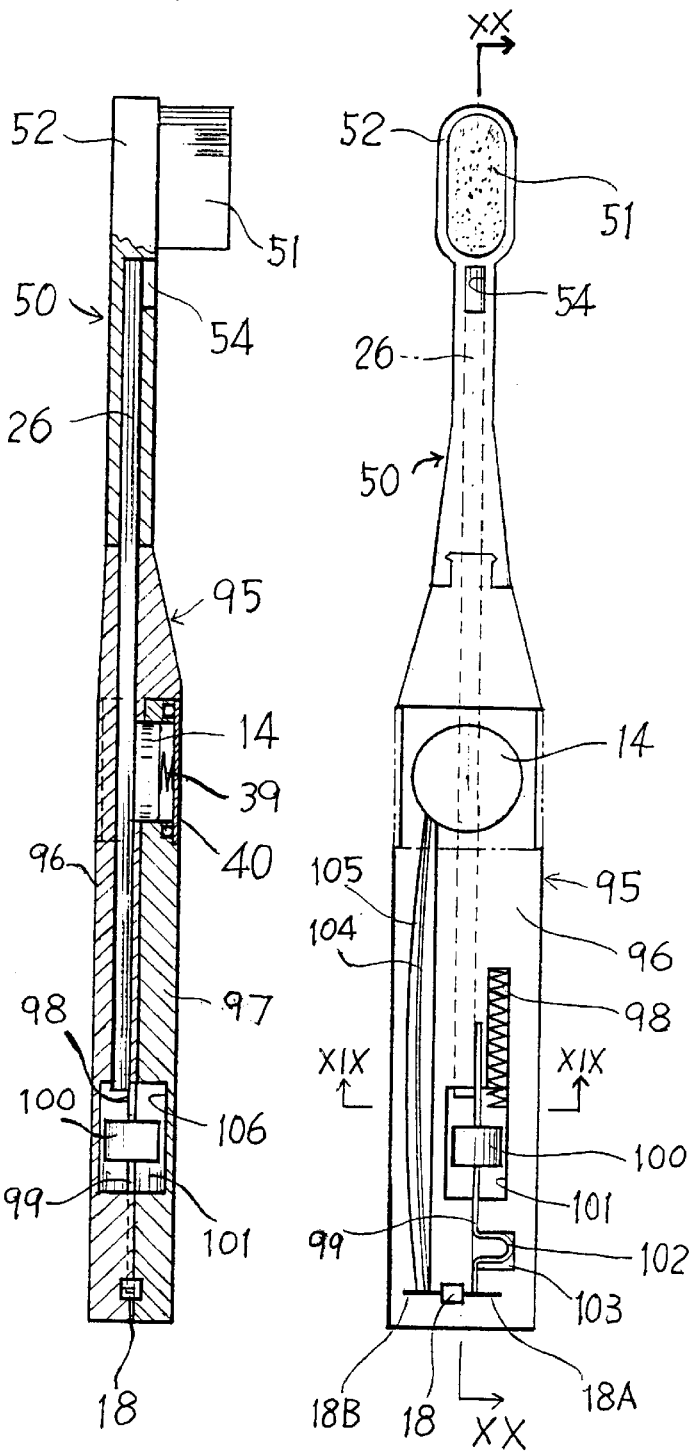

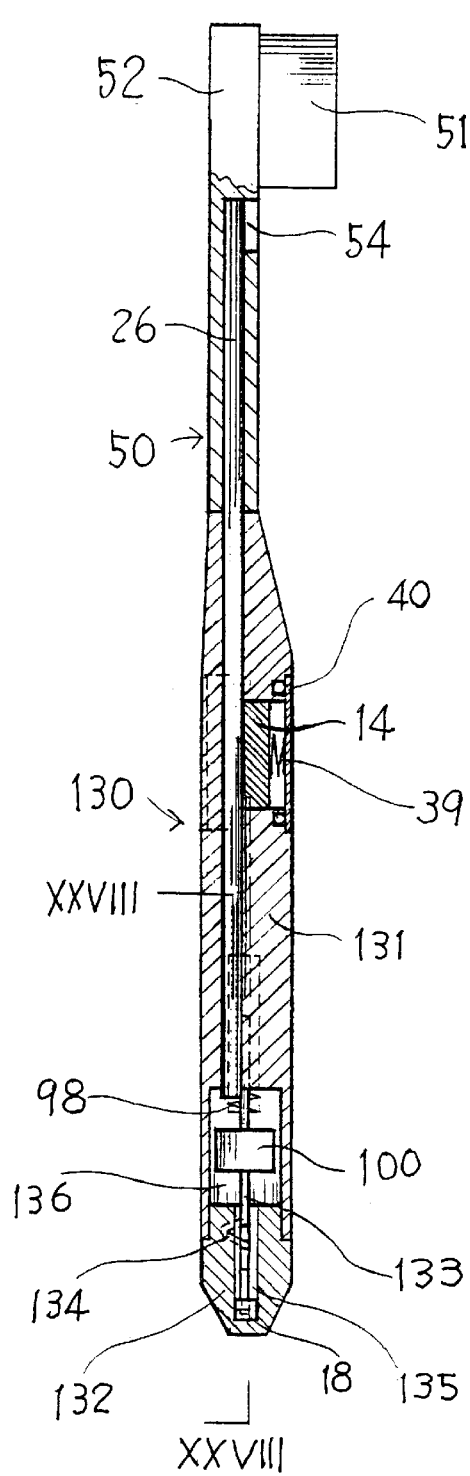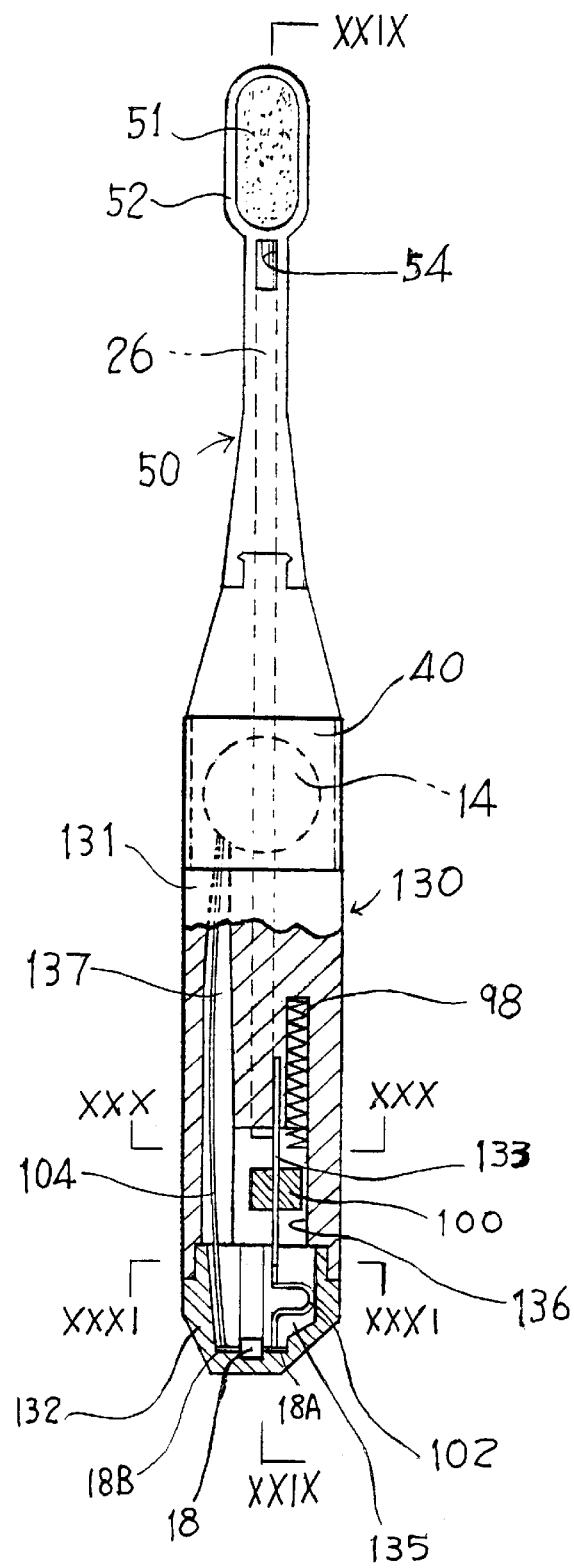
FIG. 29
FIG. 28

FIG.35
FIG.34
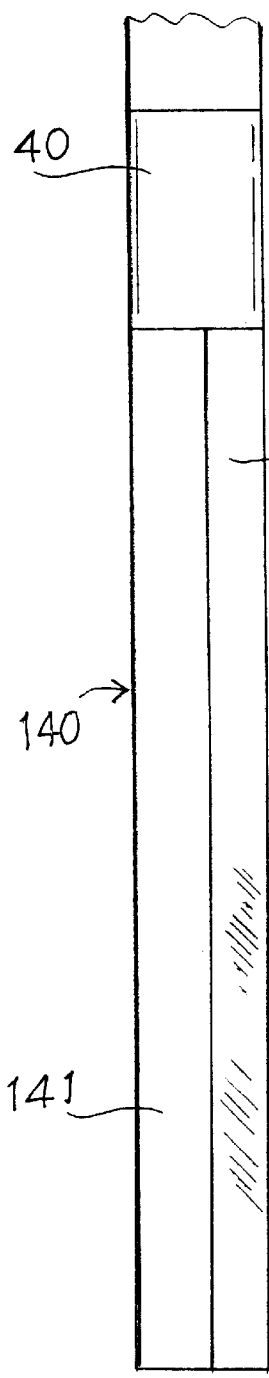
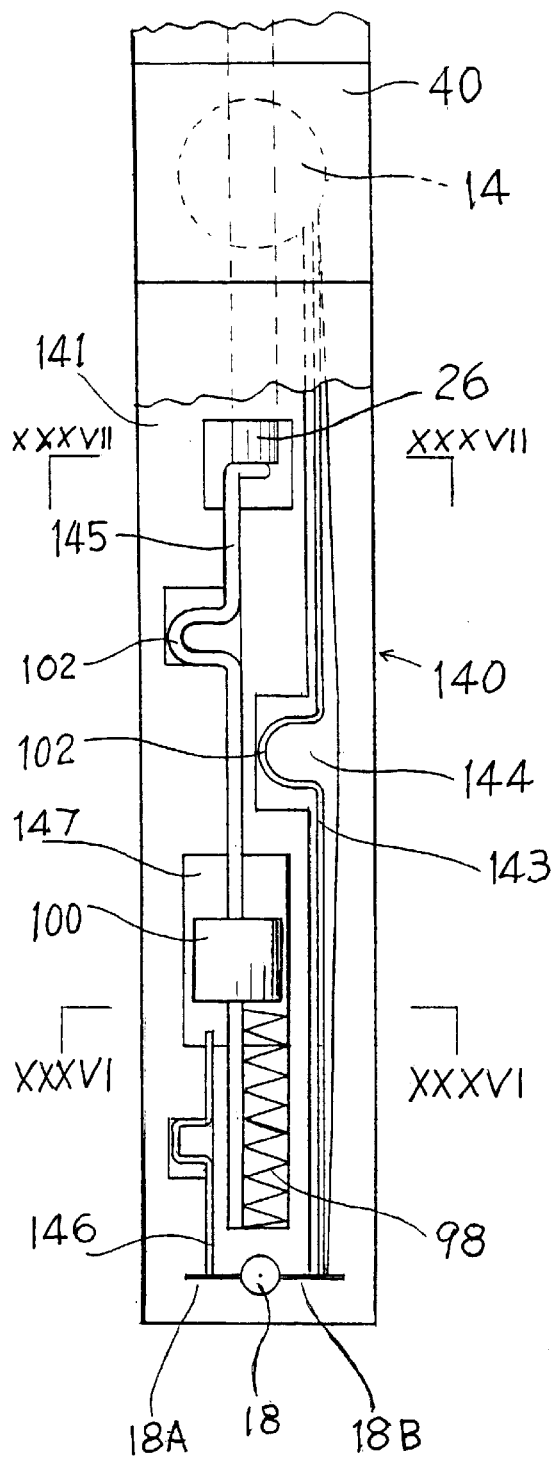

TOOTHBRUSH

BACKGROUND OF THE INVENTION

1. Field of the Invention

The present invention relates to a toothbrush capable of easily testing the effectiveness of a battery contained in the toothbrush used for tooth brushing using the battery, for example, an ion toothbrush which removes plaques more effectively and exhibits an improved brushing effect by passing an electric current between the teeth and toothbrush.

2. Description of the Related Art

There have been various proposals for an ion toothbrush which effectively removes plaques using an electrical potential gradient and exhibits an improved brushing effect by containing a battery in a handle of the toothbrush and by passing a weak electric current between a user's teeth and brush bristles of the toothbrush through the hand of the user holding the handle.

With this type of ion toothbrush, the supply voltage has to be kept at a given value in order to maintain the above-mentioned effect. Accordingly, with the type of toothbrush containing a power source such as a battery in its handle, it is necessary to test the supply voltage periodically. Japanese Patent Gazette No. 2676708 describes an ion toothbrush capable of testing the supply voltage. The toothbrush described in this patent gazette is structured in a manner such that a light emitting diode and a sounding device are provided, which operate when an electric current of 50 μA at minimum flows within a user's mouth. The light emitted from the light emitting diode can be confirmed from outside of the toothbrush. As the light emitting diode and the sounding device operate, it is easy to confirm whether the supply voltage is maintained at a given value.

However, the toothbrush described in the above-mentioned patent gazette is composed of a plurality of electronic parts which always cause the emission of light and sound while a user is brushing his teeth. Therefore, there is a problem in that it is difficult to make such a toothbrush widespread as a daily product.

Japanese Patent Laid-Open (Kokai) Publication No. Hei 2-309908 describes anion toothbrush which has an illuminant caused to emit light by turning on a switch only when a user wants to test the supply voltage.

The ion toothbrush described in Japanese Patent Laid-Open (Kokai) Publication No. Hei 2-309908 has the advantageous effect of being able to easily test the supply voltage without unnecessary battery drain. However, it still has room for further improvement with regard to simplification of the assembling steps.

SUMMARY OF THE INVENTION

The present invention aims at solving the above-described conventional problems. It is an object of this invention to provide a toothbrush which can cause the flashing of an illuminant by using a switch in order to test the effectiveness of a battery, which can reduce the battery drain caused by such testing, and of which assembling steps are simplified.

In order to achieve this object, this invention provides an ion toothbrush comprising:

a head with brush bristles implanted therein;

a handle for a user to hold; and a battery received in the handle, wherein one electrode of the battery is conductively connected with the external surface of the handle and the other electrode of the battery is conductively connected with the vicinity of the implanted area of the brush bristles at the head. The ion toothbrush further comprises:

an illuminant with its one terminal connected to one electrode of the battery and with its other terminal connected to the other electrode of the battery;

a conductive spindle capable of conductively connecting the other electrode of the battery with the vicinity of the implanted area of the brush bristles and also capable of conductively connecting with the other terminal of the illuminant; and a switch for opening and closing an electric circuit including the illuminant, the conductive spindle, and the battery.

The switch has a switch knob, and it is possible to close the electric circuit by pressing the switch knob.

The switch is located at a position somewhere between one electrode of the battery, one terminal of the illuminant, the illuninant, the other terminal of the illuminant, the conductive spindle, and the other electrode of the battery.

As the switch knob is pressed, the switch can cause the conductive spindle to conductively connect with the other terminal of the illuminant.

The handle can be composed by comprising: a handle body with a parts storage space formed therein; and a closing cover for covering the parts storage space.

The switch knob can be formed integrally with the closing cover.

The switch knob can be composed of an elastic displacement member formed integrally with the closing cover.

The closing cover can have a switch knob hole formed therein for fittingly setting the switch knob.

The closing cover can have a battery hole formed therein, which can expose one electrode of the battery.

A light transmitting part capable of transmitting light generated by the illuminant can be provided at least at a part of the switch knob.

The closing cover can be made of a light transmittable material capable of transmitting light generated by the illuminant.

The parts storage space can receive at least a part of the battery, the illuminant, both terminals of the illuminant, and the switch.

Parts placed in the parts storage space can be secured by closing the handle body with the closing cover.

At least a part of the conductive spindle can be exposed to the parts storage space.

The ion toothbrush can further comprise:

a first connector for electrically connecting one electrode of the battery with one terminal of the illuminant; and a second connector for electrically connecting the other electrode of the battery with the other terminal of the illuminant, wherein at least one of the first and second connectors can electrically connect, because of its elasticity, with the battery.

One end of the first connector can be secured to the handle and the other end of the first connector can be urged by its elasticity toward one electrode of the battery.

The first connector can be composed of a round bar with a substantially circular cross section and with its one end bent to be placed in and secured to a first groove formed in the handle.

The second connector can be urged by its elasticity toward the conductive spindle, thereby electrically connecting with the other electrode of the battery.

One end of the second connector can be secured to the handle.

The second connector can be composed of a round bar with a substantially circular cross section and with its one end bent to be placed in and secured to a second groove formed in the handle.

The first connector can be electrically connected through a wiring board to one terminal of the illuminant, the second connector can be electrically connected through the wiring board to the other terminal of the illuminant, and both terminals of the illuminant can be electrically connected to the wiring board by means of an urging force of a conductive elastic member.

The handle can comprise a handle body with a parts storage space formed therein, and a cover for closing the parts storage space, and the parts storage space can receive at least the first and second connectors, the wiring board, the elastic member, and the illuminant, and the first and second connectors, the wiring board, the elastic member, and the illuminant can be secured by closing the handle body with the cover.

The first connector can be urged by its elasticity toward a conductive member electrically connected with one electrode of the battery, and the first connector thereby electrically connects with such one electrode.

Moreover, this invention provides an ion toothbrush comprising:

a head with brush bristles implanted therein;

a handle for a user to hold; and a battery received in the handle, wherein one electrode of the battery is conductively connected with the external surface of the handle and the other electrode of the battery is conductively connected with the vicinity of the implanted area of the brush bristles at the head, and the ion toothbrush further comprises:

an illuminant or a sounding member, or both of them, with its one terminal connected to one electrode of the battery and with its other terminal connected to the other electrode of the battery; and a switch for opening and closing an electric circuit including either the illuminant or the sounding member, or both of them, and the battery, wherein the switch has a movable member capable of moving with reciprocal motion of the handle, and the electric circuit is opened or closed in accordance with the movement of the movable member.

The movable member can be composed of a rolling member or a sliding member. Moreover, the sliding member can move as it is supported by a slide spindle. Furthermore, the slide spindle can be made of a conductive material.

The handle can comprise a handle body with a parts storage space formed therein, and a closing cover for closing the parts storage space.

The other electrode of the battery can be conductively connected with the vicinity of the implanted area of the brush bristles by means of a conductive spindle.

The parts storage space can receive at least a part of the battery, the illuminant, both terminals of the illuminant, and the movable member.

A battery hole capable of exposing one electrode of the battery can be formed in the closing cover.

At least a part of the closing cover can be made of a light transmittable material capable of transmitting light generated by the illuminant.

Moreover, this invention provides an ion toothbrush wherein flashing of an illuminant or sounding of a sounding member, or both of them causes changes in electric current and voltage supplied to a circuit where an electric current passes from brush bristles, and through a user's teeth, gum, and body, a handle surface terminal, one electrode of a battery, and the other electrode of the battery, and back to the brush bristles.

Furthermore, this invention provides a toothbrush comprising:

a head with brush bristles implanted therein;

a handle for a user to hold; and a battery received in the handle, and the toothbrush further comprises:

an illuminant or a sounding member, or both of them, with its one terminal connected to one electrode of the battery and with its other terminal connected to the other electrode of the battery; and a switch for opening and closing an electric circuit including either the illuminant or the sounding member, or both of them, and the battery, wherein the switch has a movable member capable of moving with reciprocal motion of the handle, and the electric circuit is opened or closed in accordance with the movement of the movable member.

DESCRIPTION OF THE DRAWINGS

FIG. 1 is a plan view of an ion toothbrush according to Embodiment 1 of this invention.

FIG. 2 is a side view of the ion toothbrush shown in FIG. 1.

FIG. 3 is a plan view of the ion toothbrush of FIG. 1 with its conductive plate and cover removed therefrom.

FIG. 18 is a plan view of an ion toothbrush according to Embodiment 5 of this invention in the state where its conductive plate and cover are removed.

FIG. 19 is a cross section taken on line XX—XX in FIG. 18.

FIG. 20 is a cross section taken on line XIX—XIX in FIG. 18.

FIG. 28 is a plan view of an ion toothbrush according to Embodiment 7 of this invention, which is partially sectioned on line XXVIII—XXVIII in FIG. 29.

FIG. 29 is a cross section taken on line XXIX—XXIX in FIG. 28.

FIG. 34 is a plan view of an ion toothbrush according to Embodiment 8 with its cover removed therefrom.

FIG. 35 is a side view of the ion toothbrush according to Embodiment 8.

BEST MODE FOR CARRYING OUT THE INVENTION

An explanation is hereinafter given about ion toothbrushes according to embodiments of this invention with reference to the attached drawings.

Embodiment 1

Figure 4:
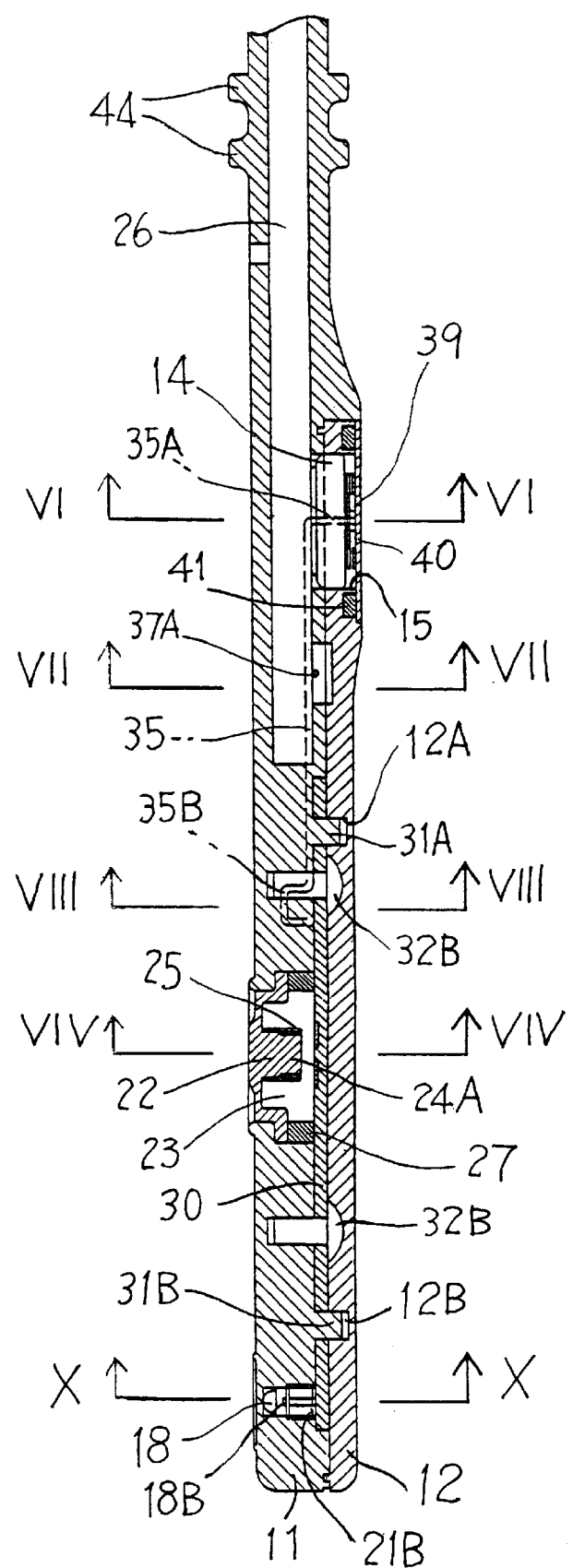
FIG. 4 is a cross section taken on line IV—IV in FIG. 3.
Figure 5:
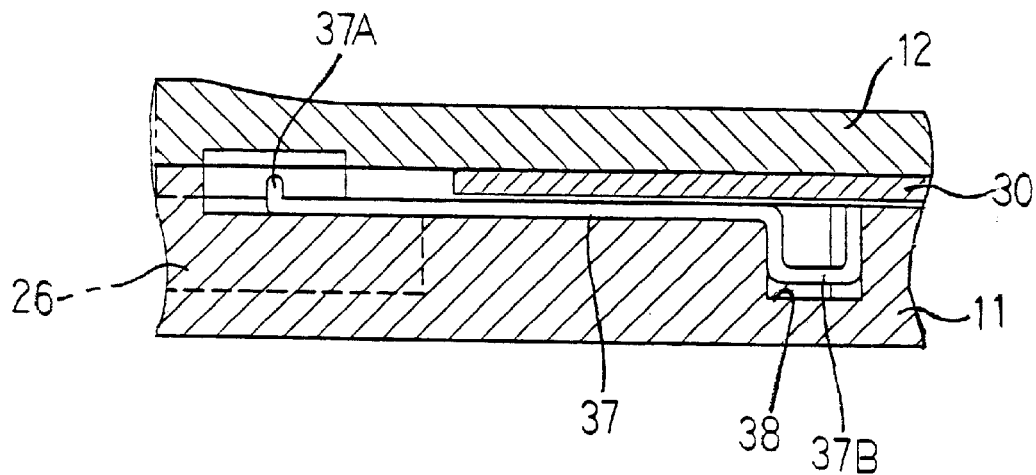
FIG. 5 is a cross section taken on line V—V in FIG. 3.
Figure 6:
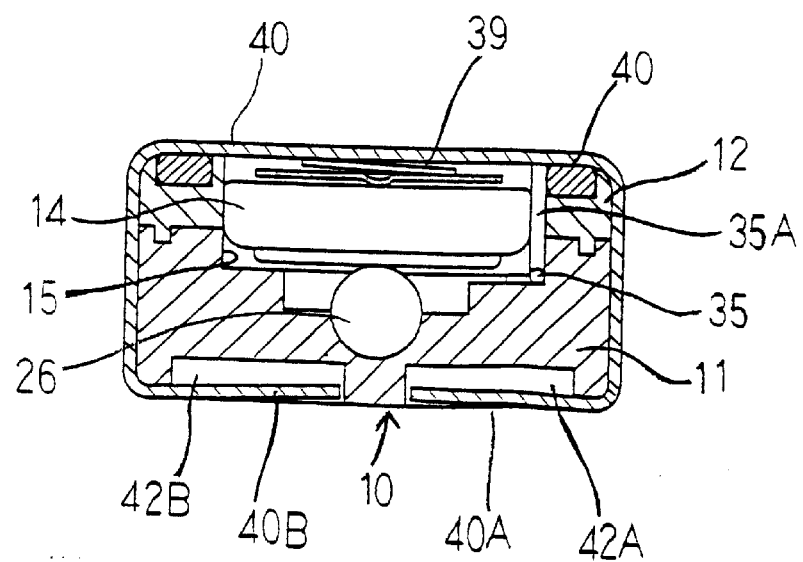
FIG. 6 is a cross section taken on line VI—VI in FIG. 4.
Figure 7:
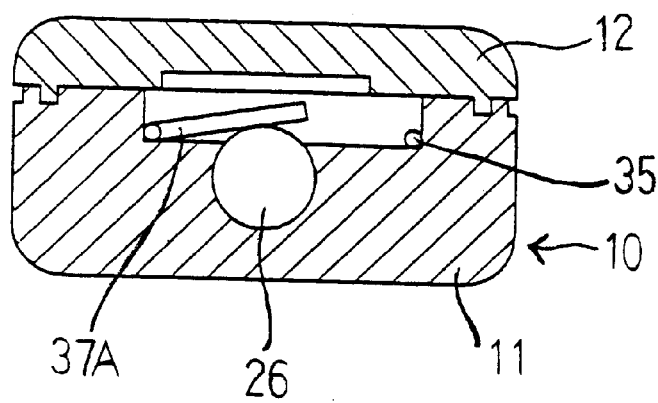
FIG. 7 is a cross section taken on line VII—VII in FIG. 4.
Figure 8:
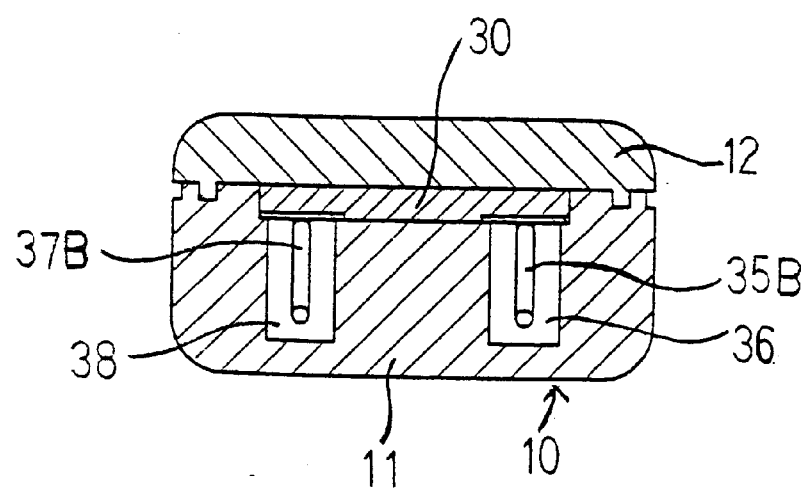
FIG. 8 is a cross section taken on line VIII—VIII in FIG. 4.
Figure 9:
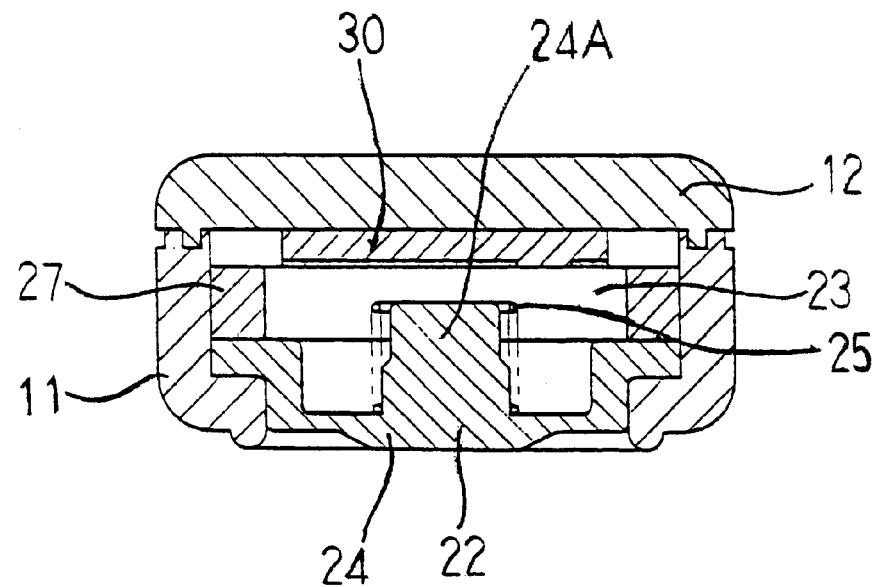
FIG. 9 is a cross section taken on line VIV—VIV in FIG. 4.
Figure 10:
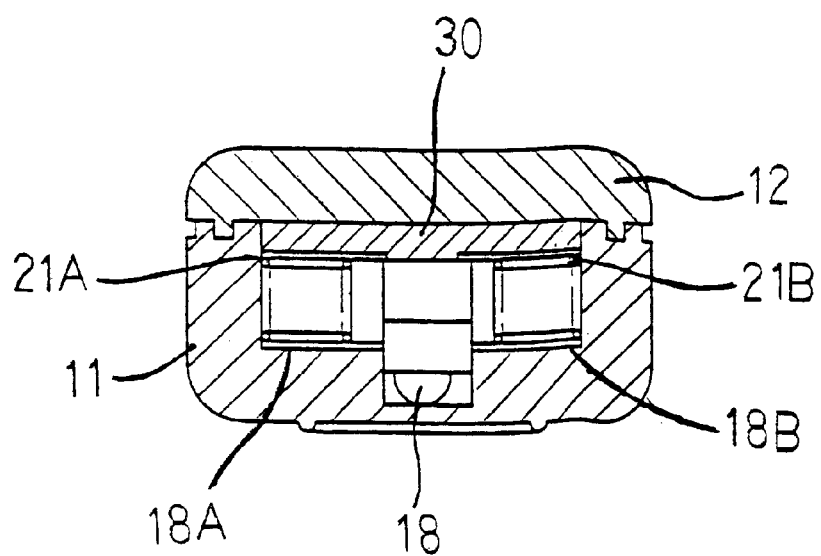
FIG. 10 is a cross section taken on line X—X in FIG. 4.

FIG. 1 is a plan view of an ion toothbrush according to Embodiment 1. FIG. 2 is a side view of the ion toothbrush shown in FIG. 1. FIG. 3 is a plan view of the ion toothbrush of FIG. 1 with its conductive plate and cover removed therefrom. FIG. 4 is a cross section taken on line IV—IV in FIG. 3. FIG. 5 is a cross section taken on line V—V in FIG. 3. FIG. 6 is a cross section taken on line VI—VI in FIG. 4. FIG. 7 is a cross section taken on line VII—VII in FIG. 4. FIG. 8 is a cross section taken on line VIII—VIII in FIG. 4, FIG. 9 is a cross section taken on line VIV—VIV in FIG. 4, FIG. 10 is a cross section taken on line X—X in FIG. 4.

In Embodiment 1, the side where brush bristles are located is called the "top end side," the opposite side is called the "base end side," the right side facing the top end side is called the "right side," and the side opposite to the right aide is called the "left side."

As shown in FIGS. 1 through 10, the ion toothbrush according to Embodiment 1 comprises a handle 10 for a user to hold, and a head 50 which is provided at the handle in a freely attachable and detachable manner and which has brush bristles 51 implanted therein.

The handle 10 comprises a handle body 11 which receives parts described later in detail, and a cover 12 which is provided on the surface of the handle body 11 with the parts received therein and which closes the handle body 11.

The handle body 11 has a battery receiving hole 15 for receiving a battery 14, which is made at a substantially center portion of its surface. This battery receiving hole 15 receives, for example, a disc-shaped lithium cell, As described later in detail, one electrode (e.g., positive electrode) of this battery 14 is connected to one end 18B of an LED 18, and the other electrode (e.g., negative electrode) of the battery 14 is connected to a spindle 26.

At the center bottom portion of the battery receiving hole 15, a part of the spindle 26 is exposed, which is made of a conductive material and which is placed at the substantially midsection of the handle body 11 in its lengthwise direction. The exposed part of the spindle 26 contacts the other electrode of the battery 14, thereby establishing the electrical connection. The spindle 26 extends within the handle body 11 in a lengthwise axial direction toward the top end side, and further extends beyond the top end of the handle body 11, and ends before reaching the brush bristles 51 when the head 50 is mounted on the handle 10. The base end side of the spindle 26 extends beyond the battery 14 and further extends until it ends before reaching the top end side of a wiring board 30 as described later in detail.

On the base end surface of the handle body 11, an illuminant receiving hole 19 is made for receiving an illuminant. This illuminant receiving hole 19 receives, for example, an LED (light emitting diode) 18. Both terminals 18A and 18B of the LED 18 are electrically connected through springs 21A and 21B made of a conductive material to the wiring board 30 described later in detail. In other words, both terminals 18A and 18B are certainly connected with and secured to the wiring board 30 by the pressing force of the springs 21A and 21B. Accordingly, it is possible to establish the electrical connection between both terminals 18A and 18B of the LED 18 and the wiring board 30 without conducting welding such as soldering, thereby enabling the simplification of the assembling steps. The bottom of the illuminant receiving hole 19 is made semitransparent so that when the LED 18 emits light, the bottom will transmit the light.

A substantially intermediate portion of the handle body 11 between the battery 14 and the LED 18 is made slightly thicker than other portions. At this intermediate portion, a switch receiving hole 23 in a substantially cylindrical shape is made through the handle body 11 in order to receive a switch 22 for opening and closing an electric circuit including the battery 14 and the LED 18. (The electric circuit will be described later in detail.)

The switch 22 placed in the switch receiving hole 23 is formed in a substantially disc shape with an elastic material such as rubber. The switch 22 comprises: a switch knob 24 with a substantially E-shaped cross section (ref. FIG. 9); a spring 25 which is made of a conductive material and which is provided on a convex part 24A formed at the center of the switch knob 24; and a ring-shaped spacer 27 provided between the periphery of the switch knob 24 and the wiring board 30.

This switch 22 is provided in a manner such that the switch knob 24 slightly projects out of the surface (this side shall be hereinafter referred to as the "lower part," "lower side," or "bottom face") opposite to the face with a cover 12 for the handle body 11 provided thereon (this side shall be hereinafter referred to as the "upper part" or "upper side"). Pushing the projected part into the handle body 11 causes the switch knob 24 to deform elastically, thereby causing the spring 25 to contact the wiring board 30 and then forming a closed circuit.

Under normal conditions where the switch 22 is not pushed, the contact of the switch knob 24 and the spring 25 with the wiring board 30 is blocked by the existence of the spacer 27. Moreover, the switch 22 is secured within the switch receiving hole 23 in the handle body 11 by the existence of the wiring board 30 and the spacer 27.

Furthermore, as the switch 22 is located closer to the midsection of the handle 10 rather than to the base end, for example, when the ion toothbrush is not used, the switch 22 will not be turned on even if the ion toothbrush is left with its base end side down.

Specifically as shown in FIGS. 3 and 9, the wiring board 30 is located above the LED 18 and the switch 22. The portion of the wiring board 30 facing the spring 25 provided on the switch knob 24 constitutes a contact with the switch. In other words, a wiring pattern of this portion is in the state not electrically connected (the wiring being disconnected) under normal conditions, and pushing the switch knob 24 causes the spring 25 to touch the contact with the switch, thereby forming the closed circuit and turning on the LED 18. This wiring board 30 is secured to the handle body 11 by convex parts 31A and 31B, which project out of the handle body 11 and pierce through the wiring board 30, and by screws 32A and 32B.

Between the wiring board 30 and the battery 14 and on the right side facing the top end of the handle body 11, there is a first connector 35 with its one end in contact with one electrode (e.g., positive electrode) of the battery 14 and with its other end in contact with a specified position of the wiring board 30, thereby electrically connecting the battery 14 and the wiring board 30.

This first connector 35 is composed of a round bar with a substantially circular cross section, which is made of a conductive elastic material, As specifically shown in FIGS. 4, 6 and 8, one end 35A of the first connector 35 in contact with one electrode of the battery 14 is bent in a substantially L shape. On the other hand, as specifically shown in FIGS. 4 and 8, the other end 35B in contact with the wiring board 30 is bent in a substantially C shape in a direction opposite to the bend direction of the L-shaped end 35A. This C-shaped end 35B is received in and secured to a first groove 36 formed in the handle body 11. This causes the first connector 35 to flex elastically from side to side of the handle body 11 as shown in FIG. 3, thereby elastically pressing the end 35A toward the outside face of the battery 14. Accordingly, the first connector 35 can be made certainly in contact with and be secured to one electrode of the battery 14. Moreover, the other end 35B of the first connector 35 is pressed against the wiring board 30 from above, and they are thereby made certainly in contact with each other. As pressed by the wiring board 30, the position of the first connector 35 is secured. As described above, it is possible to securely establish the electrical connection between the first connector 35, the battery 14, and the wiring board 30 without conducting welding such as soldering. Accordingly, it is possible to simplify the assembling steps.

Between the wiring board 30 and the battery 14 and on the left side facing the top end of the handle body 11, there is a second connector 37 with its one end in contact with the base end of the spindle 26 and with its other end in contact with a specified position of the wiring board 30, thereby establishing the electrical connection between the spindle 26 and the wiring board 30. This second connector 37 is composed of a round bar with a substantially circular cross section, which is made of a conductive elastic material.

As specifically shown in FIGS. 4, 7 and 8, one end 37A of the second connector 37 in contact with the base end of the spindle 26 is bent in a substantially L shape. On the other hand, the end 37B in contact with the wiring board 30 is bent in a substantially C shape in a direction perpendicular to the bend direction of the end 37A. This C-shaped end 37B is received in and secured to a second. groove 38 formed in the handle body 11. This causes the end 37A of the second connector 37 to elastically press the spindle 26 downwardly from above. Accordingly, the second connector 37 can be made certainly in contact with and be secured to the spindle 26. Moreover, the other end 37B of the second connector 37 is pressed against the wiring board 30 from above, and they are thereby made securely in contact with each other. As pressed by the wiring board 30, the position of the second connector 37 is secured. As described above, it is possible to securely establish the electrical connection between the second connector 37, the spindle 26, and the wiring board 30 without conducting welding such as soldering. Accordingly, it is possible to simplify the assembling steps.

In Embodiment 1, the first connector 35 and the second connector 37 are composed of round bars, which have the advantage of easy processing.

Along the periphery of the portion of the handle body 11 where the battery 14 is placed, there is provided a conductive plate 40 which serves as a terminal of the battery 14. This conductive plate 40 is secured to the handle body 11 by covering a specified position of the handle body 11 with a conductive member with a substantially U-shaped cross section and by bending its both open ends 40A and 40B inwardly to make them engage with engagement grooves 42A and 42B formed in the handle body 11.

Between the battery 14 and the conductive plate 40, there is a plate spring 39 made of a conductive material for causing the battery 14 and the conductive plate 40 to contact each other by means of its elasticity and for certainly establishing the electric connection between them. Moreover, between the battery 14 and the conductive plate 40, there is a seal member 41 tan O-ring in Embodiment 1) for keeping the battery 14 watertight.

On the end face of the handle body 11 where the spindle 26 extends out, an engagement part 43 is formed for securing the head 50 in a freely attachable and detachable manner. Reference numeral 44 indicates steps for preventing saliva or dentifrice from dripping down while brushing teeth.

The cover 12 closes the storage space for receiving various parts described above, In the inner surface of the cover 12, holes 12A and 12B are formed for engaging with the convex parts 31A and 31B formed on the handle body 11. The positioning of the cover 12 is conducted as the convex parts 31A and 31B respectively engage with the holes 12A and 12B, and the cover 12 is then secured to the handle body 11 by, for example, ultrasonic welding. This fixation of the cover 12 makes the various parts received in the handle body 11 more certainly positioned and secured.

The head 50 comprises: an implanted area 52 with brush bristles 51 implanted therein; and a shank extending in a constricted manner continuously from the implanted area 52. On the surface where the brush bristles 51 are implanted, and between the implanted area 52 and the shank 53, a communicating groove 54 is formed for exposing a part of the spindle 26. Moreover, inside of the shank 53, a spindle insert hole 55 is formed for inserting the spindle 26. On the base end side of the shank 53, an engagement concave 56 is formed for engaging with the engagement part 43 formed on the handle body 11.

When a user holds the handle 10 of the ion toothbrush having the above-described structure by touching the conductive plate 40 with the user's hand and brushes his teeth with the brush bristles 51, the brush bristles 51 become wet with a liquid such as saliva and the spindle 26 enters into the electrically conductive state through a liquid communicating pathway including the communicating groove 54. This causes an electric current to pass through the route starting from the battery 14, and through -the user's hand, body, and teeth, the brush bristles 51, the liquid pathway including the communicating groove 54, and the spindle 26, and back to the battery 14. Then, the electrical potential gradient can enhance the plaque removal effect and the brushing effect at the time of brushing teeth.

In order to confirm the effectiveness of the battery 14, pressing the switch 22 causes the spring 25 to contact the wiring board 30, thereby composing an electric circuit where an electric current passes from the battery 14, and through the first connector 35, the wiring board 30, the spring 21B, the LED 18, the spring 21A, the wiring board 30, the spring 25, the wiring board 30, and the second connector 37, and back to the battery 14. If the battery 14 retains given voltage, the above action causes the LED 18 to go on, which indicates that the battery 14 is effective. On the other hand, if the battery 14 has become exhausted and no longer retains given voltage, the LED 18 does not go on even if the switch 22 is pressed.

When the user stops pressing the switch 22, the elasticity of the switch knob 24 and the spring 25 causes the spring 25 to move away from the wiring board 30 and the above-describe electric circuit returns to an open circuit, and the LED 18 thereby goes off.

As described above, the ion toothbrush of this invention can easily test the supply voltage by turning on (pressing) the switch 22 whenever the user wants to do so.

Moreover, the handle 10 is divided into the handle body 11 and the cover 12. The terminal 18B of the LED 18 and the first connector 35 are caused by means of their elasticity to contact the side face of the battery 14, the wiring board 30 is held between the handle body 11 and the cover 12, and the cover 12 is then welded, thereby securing these members. Accordingly, it is possible to certainly electrically connect, locate, and secure these members without conducting laborious welding such as soldering. Therefore, it is possible to simplify the assembling steps.

Embodiment 1 described an ion toothbrush with the head 50 which is separable from the handle 10. However, as a matter of course, the structure of the ion toothbrush of this invention is not limited to the above-described separable structure, and the head and the handle may be integrally formed.

Moreover, Embodiment 1 described a case where the electric connection between the first connector 35 and one terminal 18B of the LED 18 and the electric connection between the second connector 37 and the other terminal 18A of the LED 18 are established through the wiring board 30 and the springs 21A and 21B. However, without limitation to such means, the electric connections may be established by using other connecting means.

Furthermore, Embodiment 1 described a case where the first connector 35 and the second connector 37 are composed of round bars with substantially circular cross sections. However, without limitation to such a shape, the shape of the first and second connectors may be determined arbitrarily as long as they can certainly contact the battery 14 or the spindle 26 by means of their elasticity. For example, the shape of their cross sections can be determined arbitrarily as substantially oval, polygonal, or the like.

Also, Embodiment 1 described a case where the second connector 37 is caused to contact the spindle 26. However, without limitation to such a structure, the second connector 37 may be structured in a manner such that it is caused to contact the other electrode of the battery 14 directly.

Moreover, the position of the switch 22 is not limited to that described in Embodiment 1, and the switch 22 may be located at any position somewhere between one electrode of the battery 14, one terminal 18A or 18B of the LED 18, the LED 18, the spindle 26, and the other electrode of the battery 14.

Embodiment 2

An explanation is hereinafter given about an ion toothbrush according to Embodiment 2 of this invention with reference to the relevant drawings.

Figure 11:
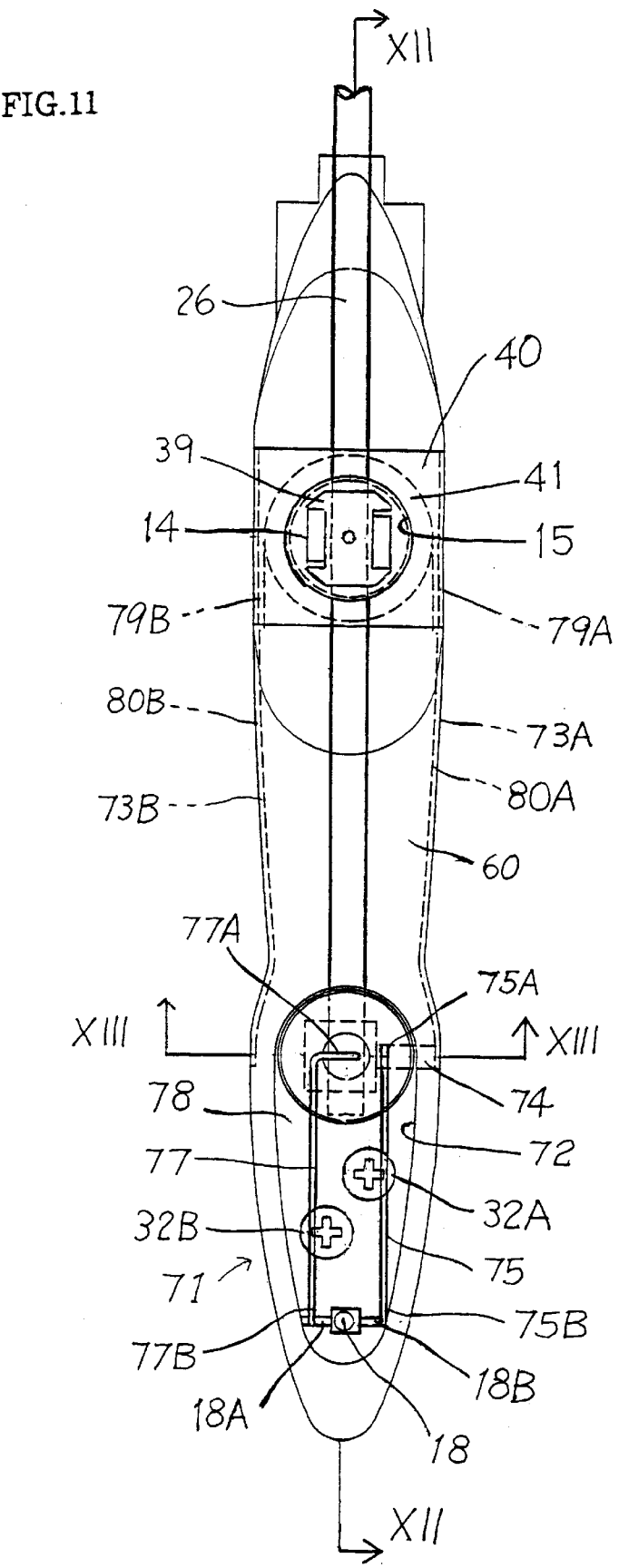
FIG. 11 is a plan view of an ion toothbrush according to Embodiment 2 of this invention.
Figure 12:
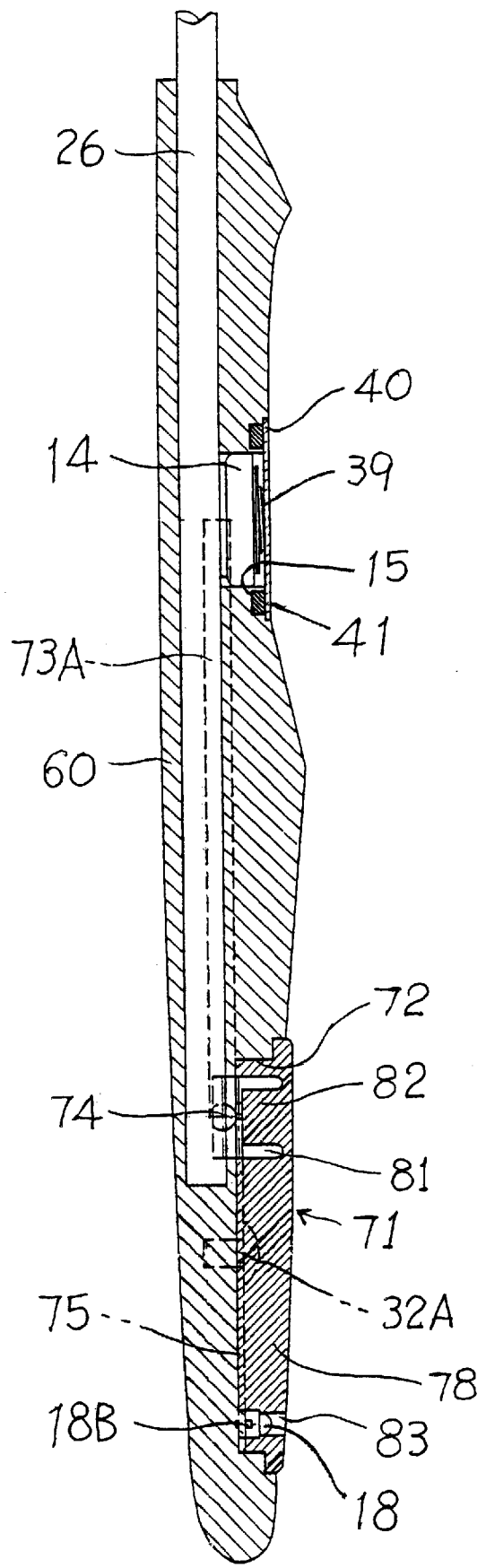
FIG. 12 is a cross section taken on line XII—XII in FIG. 11.
Figure 13:
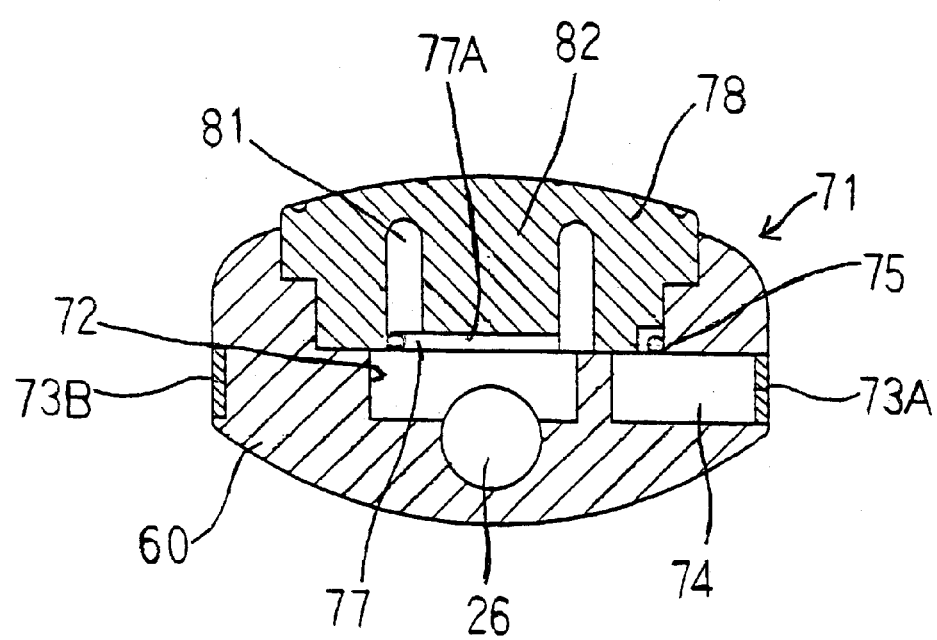
FIG. 13 is a cross section taken on line XIII—XIII in FIG. 11.

FIG. 11 is a plan view of an ion toothbrush according to Embodiment 2. FIG. 12 is a cross section taken on line XII—XII in FIG. 11. FIG. 13 is a cross section taken on line XIII—XIII in FIG. 11. FIG. 11 is illustrated as it a handle, a conductive plate, and a switch knob are transparent in order to clearly show the arrangement of parts. Members used in Embodiment 2 which are similar to those of the ion toothbrush of Embodiment 1 are given the same reference numerals as in Embodiment 1, and any detailed description thereof is omitted.

As shown in FIGS. 11 through 13, the ion toothbrush according to Embodiment 2 comprises a stream-line handle 60 for a user to hold, and the head 50 as described in Embodiment 1.

The handle 60 has a battery receiving hole 15 for receiving a battery 14 at the substantially center part of its surface, and also has a storage hole 72 for receiving a switch 71 and an LED 18 on its base end side. Moreover, on both sides extending in the lengthwise direction of the handle 60, film member receiving holes 80A and 80B are formed for receiving film members 73A and 73B described later in detail. The top ends of these film member receiving holes 80A and 80B are formed as concave parts 79A and 79B having the depth corresponding to the thickness of the conductive plate 40.

The film members 73A and 73B are composed of films, tapes or the like made of a conductive material and are received and placed in the film member receiving holes 80A and 80B in the handle 60. The film members 73A and 73B have the same thickness as the depth of the film member receiving holes 80A and 80B. When the film members 73A and 73B are placed in the film member receiving holes 80A and 80B, the height of the film members 73A and 73B become equal to the height of the side face of the handle 60. In other words, the film members 73A and 73B become flush with the side face of the handle 60. The top ends of the film members 73A and 73B are respectively received in the concave parts 79A and 79B and are covered with the conductive plate 40, and both of the film members 73A and 73B are thereby electrically connected with the conductive plate 40. Since the concave parts. 79A and 79B have the depth equal to the thickness of the film members 73A and 73B plus the thickness of the conductive plate 40, when the conductive plate 40 is placed, the external surface of the handle 60 becomes flush with the surface of the conductive plate 40. Both of the film members 73A and 73B are electrically connected through the conductive plate 40 with one electrode of the battery 40.

The structure of the spindle 26 placed within the handle 60 is similar to that as described in Embodiment 1, except that the base end of the spindle 26 extends and reaches the switch 71.

At the handle 60 in the vicinity of the base end of the spindle 26, a conductive pin 74 is formed which projects perpendicularly to the lengthwise direction of the spindle 26 toward the base end of the spindle 26. The pin 74 ends before, and does not contact, the spindle 26. Moreover, the pin 74 is connected with the film member 73A. Furthermore, the pin 74 is connected with the film member 73A. This structure causes the pin 74 to be electrically connected through the film member 73A and the conductive plate 40 to one electrode of the battery 14.

Between the terminal 18B of the LED 18 and the pin 74, there is a first connector 75 made of a conductive elastic material. One end 75A of the first connector 75 on the top end side is in contact with the pin 74, while the other end 75B thereof on the base end side is in contact with the terminal 18B of the LED 18.

The first connector 75 is composed of a round bar with a substantially circular cross section, and is formed in the shape with its ends 75A and 75B bent downward and with its substantially center part slightly bent upward, and is fastened at the handle 60 with a screw 32A. Because of this structure and the elasticity of the first connector 75, the first connector 75 flexes elastically, thereby causing the end 75A to press the pin 74 from above and also causing the end 75B to elastically press the terminal 18B of the LED 18 from above. Accordingly, it is possible to make the first connector 75 certainly become in contact with and be secured to one electrode of the battery 14 through the pin 74, the film member 73A, and the conductive plate 40. It is also possible to make the end 75B of the first connector 75 certainly become in contact with and be secured to the terminal 18B of the LED 18.

Between the terminal 18A of the LED 18 and the base end of the spindle 26, there is a second connector 77 made or a conductive elastic material. The second connector 77 is composed of a round bar with a substantially circular cross section, which is made of a conductive elastic material, One end 77A of the second connector 77 on the top end side is bent in a substantially L shape and projects out over the base end of the spindle 26. In this state, the end 77A is not in contact with the spindle 26 as specifically shown in FIG. 13. The end 77B on the base end side is in contact with the terminal 18A of the LED 18. The second connector 77 is fastened to the handle 60 with a screw 32B.

The LED 18 can be checked from outside of the handle 60 through a window 83 opened in a switch knob 78 as described later in detail. This window 83 may be provided with a light transmittable material capable of transmitting light generated by the LED 18, or the LED 18 maybe exposed without setting anything at the window 83. As such a light transmittable material, various materials can be used such as transparent or semi-transparent plastic materials, or other resins, lens, glass, or the like.

The switch 71 is composed of: the base end of the spindle 26; the second connector 77; and the switch knob 78 fitted in a storage hole 72 for receiving the parts described above.

The switch knob 78 is made of an elastic material such as rubber and has a ring-shaped space 81 on its top end side, that is, at a position corresponding to that of the L-shaped end 77A of the second connector 77. This space 81 defines a substantially cylindrical switch part 82. The switch knob 78 is secured to the handle 60, for example, by welding or adhesion.

Upon checking the effectiveness of the battery of the ion toothbrush having the, above-described structure, pressing the switch part 82 of the switch knob 78 causes the switch part 82 to push down the end 77A of the second connector 77, thereby causing the end 77A to contact the spindle 26. This constitutes an electric circuit where an electric currant passes from the battery 14 and then through the conductive plate 40, the film member 73A, the pin 74, the first connector 75, the LED 18, the second connector 77, and the spindle 26, and then back to the battery 14. If the battery 14 retains given voltage, the above-described action causes the LED 18 to go on, which indicates that the battery 14 is effective. On the other hand, if the battery 14 has become exhausted and no longer retains given voltage, the LED 18 does not go on even if the switch part 82 of the switch knob 78 is pressed.

When the user stops pressing the switch 71, the elasticity of the switch knob 78 and the second connector 77 causes the second connector 77 to move away from the spindle 26 and the above-describe electric circuit returns to an open circuit, and the LED 18 thereby goes off.

As described above, the ion toothbrush according to Embodiment 2 can also easily test the supply voltage by pressing the switch whenever the user wants to do so.

Embodiment 2 described a case where the first connector 75 and the second connector 77 are composed of round bars. However, without limitation to such a shape, the shape of the first and second connectors may be determined arbitrarily as long as they can certainly contact the pin 74 or the spindle 26, and the terminals 18A and 18B of the LED 18 by means of their elasticity. For example, the shape of their cross sections can be determined arbitrarily as substantially oval, polygonal, or the like.

Moreover, the shape of the ends 75A and/or 75B of the first connector 75 may be changed by, for example, bending into a substantially L shape so that the first connector 75 can contact the pin 74 and the terminal 18B of the LED 18 with more certainty. The same thing can be said about the second connector 77.

In Embodiment 2, the window 83 is formed so that a user can check the light generated by the LED 18. However, without limitation to such a structure, the entire switch knob 78 may be composed of the above-mentioned light transmittable material instead of forming the window 83.

Embodiment 3

An explanation is hereinafter given about an ion toothbrush according to Embodiment 3 of this invention with reference to the relevant drawings.

Figure 14:
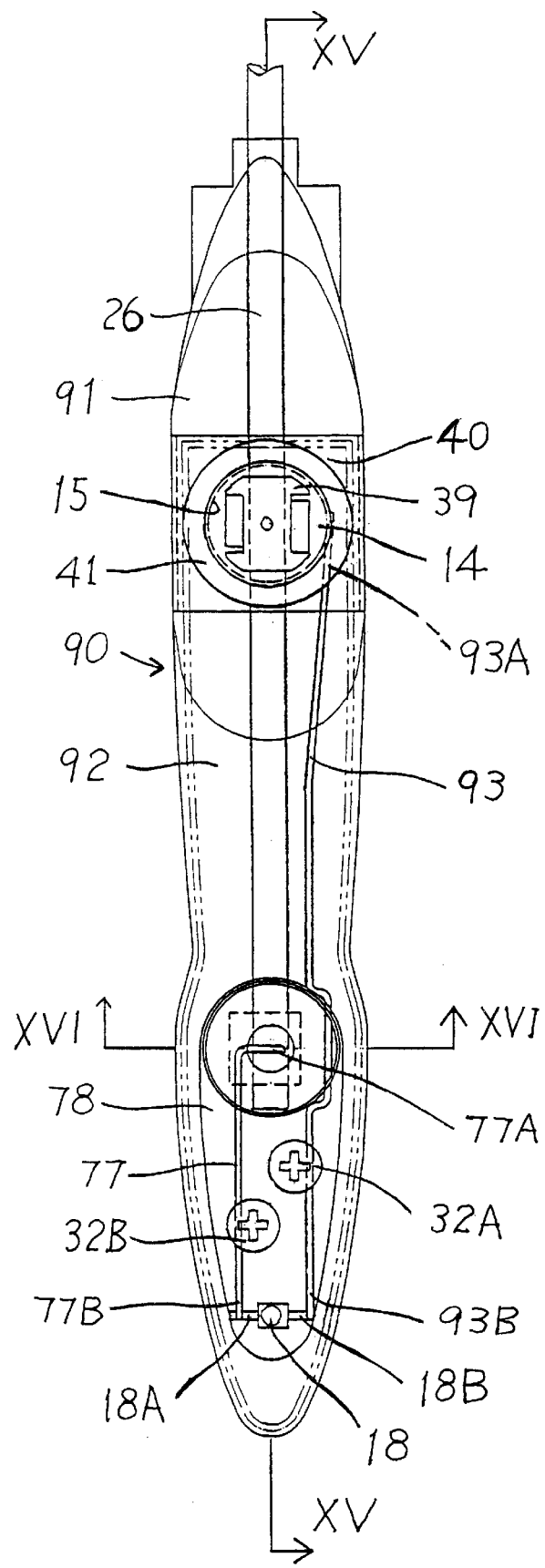
FIG. 14 is a plan view of an ion toothbrush according to Embodiment 3 of this invention.
Figure 15:
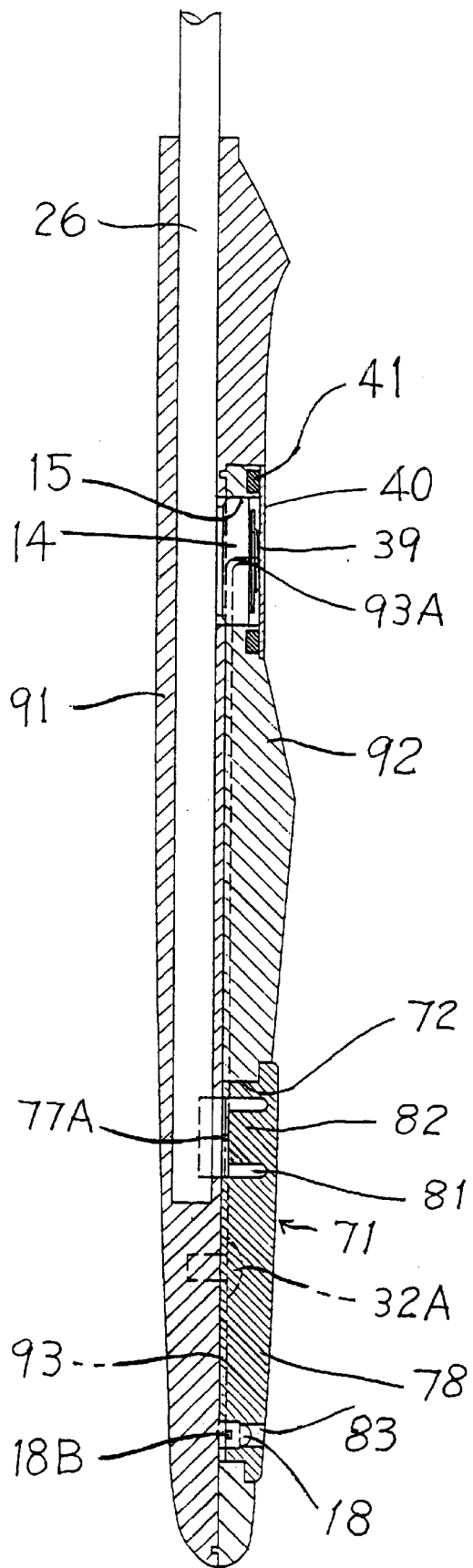
FIG. 15 is a cross section taken on line XV—XV in FIG. 14.
Figure 16:
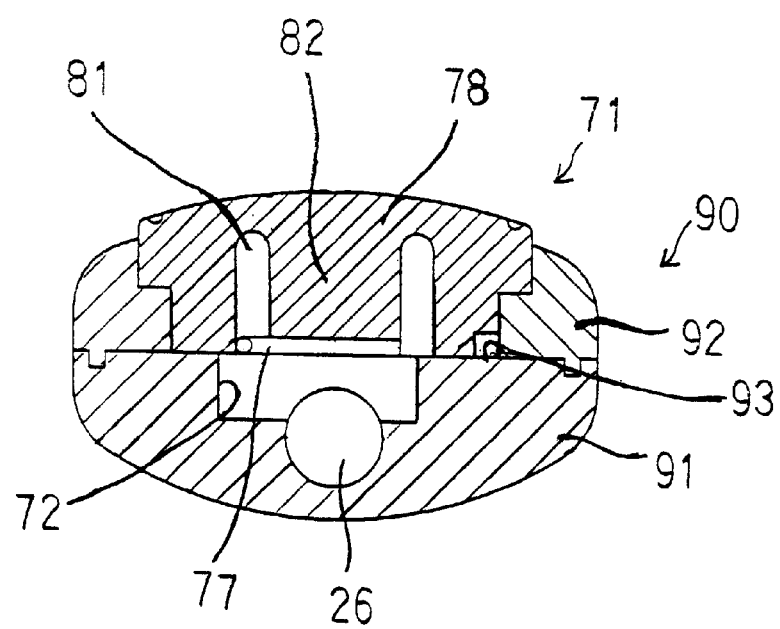
FIG. 16 is a cross section taken on line XVI—XVI in FIG. 14.

FIG. 14 is a plan view of an ion toothbrush according to Embodiment 3. FIG. 15 is a cross section taken on line XV—XV in FIG. 14. FIG. 16 is a cross section taken on line XVI—XVI in FIG. 14. FIG. 14 is illustrated as if a handle, a conductive plate, and a switch knob are transparent in order to clearly show the arrangement of parts. In Embodiment 3, members similar to those of the ion toothbrush according to Embodiment 1 or 2 are given the same reference numerals as in Embodiment 1 and 2, and any detailed description thereof is omitted.

The ion toothbrush according to Embodiment 3 is different from the ion toothbrush according to Embodiment 2 in that the handle is composed of a handle body and a cover, and one end of a first connector on the top end side is in contact with one electrode of a battery 14.

As shown in FIGS. 14 through 16, the ion toothbrush according to Embodiment 3 comprises a stream-line handle 90 for a user to hold, and the head 50 as described in Embodiment 1.

The handle 90 comprises a handle body 91 for receiving parts described later in detail, and a cover 92 which is provided on the surface of the handle body 91 with the parts received therein and which closes the handle body 91.

The handle body 91 has a battery receiving hole 15 for receiving a battery 14 at the substantially center part of its surface, and also has a storage hole 72 for receiving a switch 71 and an LED 18 on its base end side.

The structure of a spindle 26 located within the handle body 91 is similar to that as described in Embodiment 1, except that the base end of the spindle 26 extends and reaches the switch 71.

On the right side of the handle body 91 and between the battery 14 and the LED 18, there is a first connector 93 for electrically connecting one electrode of the battery 14 with one terminal 18B of the LED 18.

The first connector 93 is composed of a round bar with a substantially circular cross section, which is made of a conductive elastic material. One end 93A of the first connector 93 in contact with one electrode of the battery 14 is bent in a substantially L shape, and the first connector 93 in the vicinity of a switch part 82 is bent in a substantially U shape in order to avoid the switch part 82. The first connector 93 is fastened at the handle body 91 with a screw 32A. Because of this structure and the elasticity of the first connector 93, the first connector 93 flexes elastically, thereby causing the end 93A to elastically press the external side face of the battery 14 and also causing the other end 93B to elastically press the terminal 18B of the LED 18 from above. Accordingly, it is possible to make the first connector 93 certainly contact and be secured to one electrode of the battery 14 and the terminal 18B of the LED 18.

The cover 92 closes the base end side of the handle body 91 by using a conductive plate 40 and is secured to the handle body 91 by means of, for example, ultrasonic welding.

Upon checking the effectiveness of the battery 14 of the ion toothbrush having the above-described structure, pressing the switch part 82 of a switch knob 78 causes the switch part 82 to push down one end 77A of a second connector 77, thereby causing the end 77A to contact the spindle 26. This constitutes an electric circuit where an electric current passes from the battery 14 and then through the first connector 93, the LED 18, the second connector 77, and the spindle 26, and then back to the battery 14. If the battery 14 retains given voltage, the above-described action causes the LED 18 to go on, which indicates that the battery 14 is effective. On the other hand, if the battery 14 has become exhausted and no longer retains given voltage, the LED 18 does not go on even if the switch part 82 of the switch knob is pressed.

When the user stops pressing the switch 71, the elasticity of the switch knob 78 and the second connector 77 causes the second connector 77 to move away from the spindle 26 and the above-describe electric circuit returns to an open circuit, and the LED 18 thereby goes off.

As described above, the ion toothbrush according to Embodiment 3 can also easily test the supply voltage by pressing the switch whenever the user wants to do so.

Embodiments 2 and 3 described a stream-line handle. However, without limitation to such a shape, the shape of the handle in Embodiment 1 may be applied.

The arrangement of the respective parts of Embodiment 2 can be applied to the handle 90 of Embodiment 3.

With the ion toothbrush according to Embodiment 3, the handle 90 is divided into the handle body 91 and the cover 92, The cover 92 also has a battery receiving hole 15. The first connector 93 is caused by means of its elasticity to contact the terminal 18B or the LED 18 and the side face of the battery 14, these members are placed on a joint face of the handle body 91 with the cover 92, and the cover 12 is then welded, thereby securing these members. Accordingly, it is possible to electrically connect, locate, and secure these members with certainty without the necessity to conduct laborious welding such as soldering. Therefore, it is possible to simplify the assembling steps.

Embodiment 4

Embodiment 4 of this invention is hereinafter described with reference to the relevant drawing.

Figure 17:
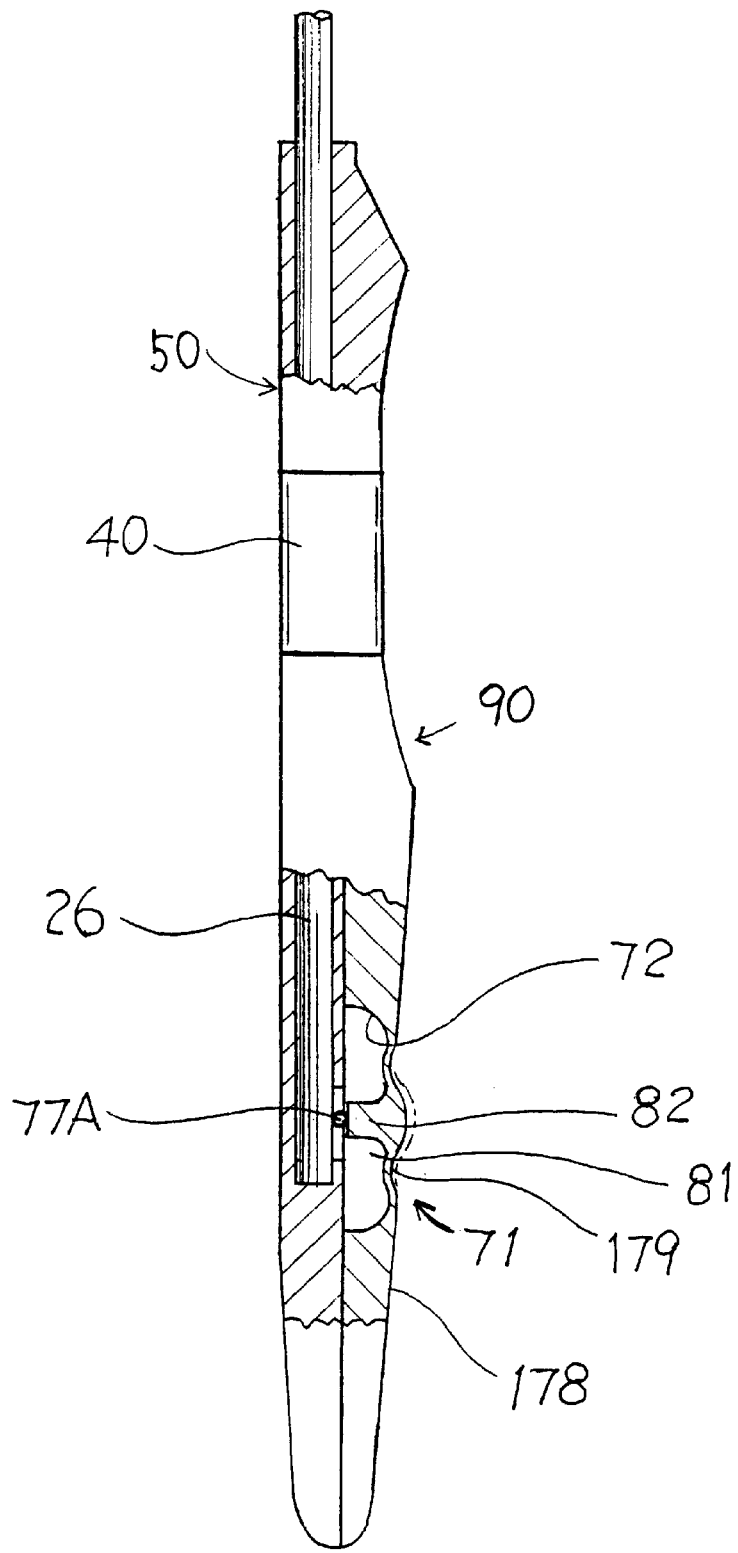
FIG. 17 is a partially sectional view of an ion toothbrush according to Embodiment 4 of this invention, which corresponds to FIG. 15.

FIG. 17 is a partially sectional view of an ion toothbrush according to Embodiment 4, which corresponds to FIG. 15.

In Embodiment 4, members similar to those of the ion toothbrush according to Embodiment 3 are given the same reference numerals as those in Embodiment 3, and any detailed description thereof is omitted.

The ion toothbrush according to Embodiment 4 is different from the ion toothbrush according to Embodiment 3 in that a switch knob and a cover are integrally formed.

As shown in FIG. 17, a cover 178 of the ion toothbrush according to Embodiment 4 has a switch part 82 integrally formed therewith by means of an accordion part 179 formed along the upper periphery of the cover 178. This cover 178 is made of a slightly elastic material. This switch part 82 pushes down one end 77A of a second connector 77 by means of the spring action of the accordion part 179, and the end 77A thereby electrically contacts the spindle 26.

In the above-described structure, it is possible to compose the entire cover 178 of a light transmittable material capable of transmitting light generated by the LED 18. If such a structure is employed, it is unnecessary to compose a window 83.

Since the switch knob and the cover are integrally formed, it is possible to reduce the number of the assembly parts and to simplify the assembling steps.

Embodiment 5

An explanation is hereinafter given about an ion toothbrush according to Embodiment 5 of this invention with reference to the relevant drawings.

FIG. 18 is a plan view of an ion toothbrush according to Embodiment 5 in the state where its conductive plate and cover are removed. FIG. 19 is a cross section taken on line XX—XX in FIG. 18. FIG. 20 is a cross section taken on line XIX—XIX in FIG. 18.

In Embodiment 5, members similar to those of the ion toothbrushes according to the above-described embodiments are given the same reference numerals as in the above-described embodiments, and any detailed description thereof is omitted.

As shown in FIGS. 18 through 20, the ion toothbrush according to Embodiment 5 comprises a handle 95 for a user to hold, and the head 50 as described in Embodiment 1.

The handle 95 comprises: a handle body 96 for receiving parts described later in detail; and a cover 97 which is provided on the surface of the handle body 96 with the parts received therein and which closes the handle body 96.

The handle body 96 receives a battery 14 and an LED 18 as in Embodiment 1. In an area slightly closer to the base end side than to the central part of the handle body 96, a storage hole 101 is made for receiving the following parts as described later in detail: a spring 98; a slide spindle 99; and a sliding member 100 as a movable member which is pierced in a manner movable relative to the slide spindle 99. Moreover, at a position more closer to the base end aide of the handle body 96, a storage hole 103 is made for receiving a bend part 102 of the slide spindle 99. Furthermore, on the left side of the handle body 96, there is a storage hole 105 for receiving a first connector 104 which electrically connects one end 18B of the LED 18 with one electrode of the battery 14.

The cover 97 has a storage hole 106 for receiving the upper part of the sliding member 100 in a movable manner. This cover 97 is made of a light transmittable material capable of transmitting light generated by the LED 18.

The first connector 104 is composed of a round bar with a substantially circular cross section, which is slightly bent arcuately. This first connector 104 is securely electrically connected, by means of is elasticity obtained by the arch bend, with the terminal 18B of the LED 18 and one electrode of the battery 14.

The slide spindle 99 is formed with a conductive material and has the bend part 102 formed in a substantially C shape at Its end on the base end side. The end of the slide spindle 99 on the base end side is securely electrically connected, by means of its elasticity obtained by the bend part 102, with the end 18A of the LED 18. This slide spindle 99 corresponds to the second connector as described in the aforementioned embodiments.

The sliding member 100 is made of a conductive material, has the slide spindle 99 pierced through at the substantially center thereof, and is mounted on the slide spindle 99 in a movable manner. This sliding member 100 moves along the slide spindle 99 with reciprocating motion of the handle 95, When the sliding member 100 moves toward the top end side of the handle 95, it presses the spring 98 located on the top end side of the storage hole 101 and can also become in contact with the base end of the spindle 26 exposed in the storage hole 101. The sliding member 100 contacting the spindle 26 is pushed back to the base end side or the handle 95 by the urging force of the spring 98, thereby releasing the contact. At this time, if the handle 95 is moved in a reciprocating manner, this reciprocating motion also moves the sliding member 100 toward the base end side of the handle 95, thereby releasing the contact between the sliding member 100 and the spindle 26.

In other words, the movement of the sliding member 100 functions as a switch.

As the sliding member 100 contacts the base end of the spindle 26 as described above, an electrical circuit is established where an electric current passes from the battery 14, and then through the first connector 104, the LED 18, the slide spindle 99, the sliding member 100, and the spindle 26, and then back to the battery 14. If the battery 14 retains given voltage, the above action causes the LED 18 to go on, which indicates that the battery 14 is effective. On the other hand, if the contact between the spindle 26 and the sliding member 100 is released, the electric circuit is opened and the LED 18 goes off. While the handle 95 continues the reciprocating motion, the above-described action causes the LED 18 to go on and off repeatedly.

As described above, the ion toothbrush according to Embodiment 5 can easily test the supply voltage when a user shakes the ion toothbrush to move the handle 95 in a reciprocating manner, thereby moving the sliding member 100.

Moreover, since it is unnecessary to provide a switch on the surface of the handle 95, it is possible to simplify the structure of the surface of the handle.

Furthermore, the ion toothbrush according to Embodiment 5 allows a low frequency fluctuating current, which is generated by the flashing of the LED 18 caused by the movement of the sliding member 100, to be utilized for brushing teeth, thereby making it possible to keep a user's mouth clean more effectively and to remove the plaque.

Additionally, if a sound generating circuit (a sounding member) for generating sound upon the closing of the above-mentioned electric circuit is connected at a desirable position of the electric circuit, it is possible to use the sound in order to check the effectiveness of the battery 14. An example of such a sound generating circuit is the circuit capable of generating electronic beeps.

It is without doubt that Embodiment 5 can achieve the same advantageous effect as that of the simplification of the assembling steps as described in the aforementioned embodiments.

Embodiment 6

An explanation is hereinafter given about an ion toothbrush according to Embodiment 6 with reference to the relevant drawings.

Figure 21:
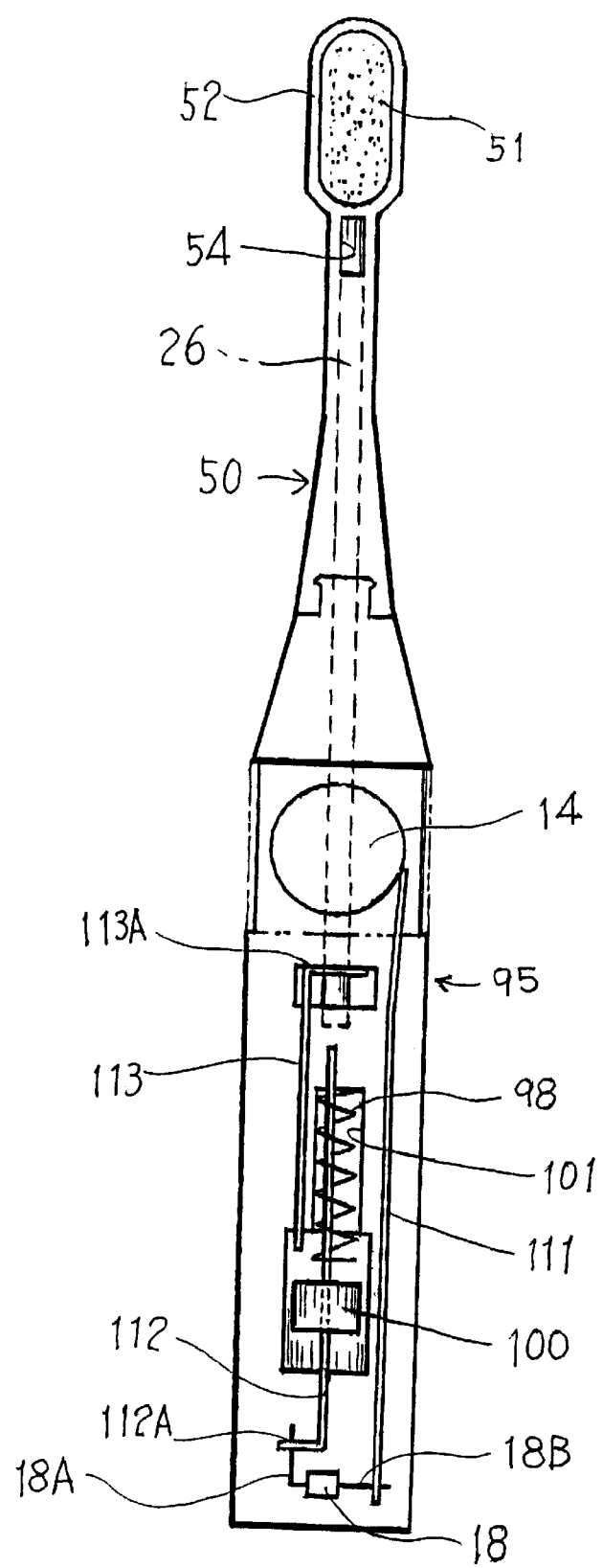
FIG. 21 is a plan view of an ion toothbrush according to Embodiment 6 of this invention.
Figure 22:
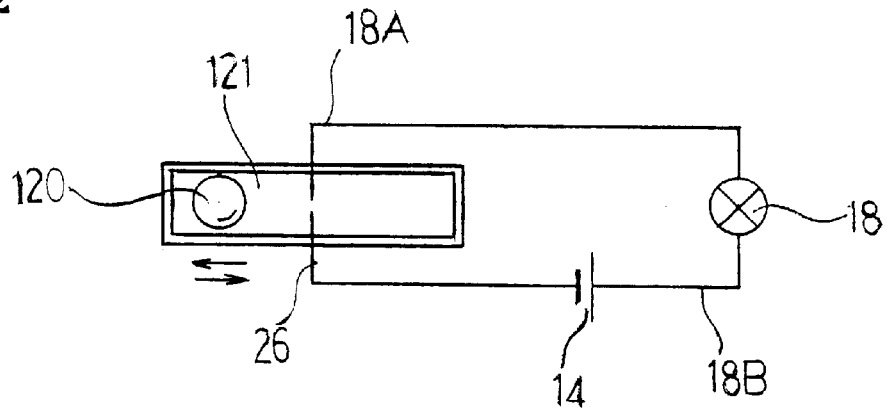
FIG. 22 is a schematic diagram of an electric circuit according to another embodiment of this invention.

FIG. 21 is a plan view of the ion toothbrush according to Embodiment 6.

In Embodiment 6, members similar to those of the ion toothbrushes according to Embodiment 5 are given the same reference numerals as in Embodiment 5, and any detailed description thereof is omitted.

The ion toothbrush according to Embodiment 6 is different from the ion toothbrush according to Embodiment 5 in that when a sliding member 100 moves toward the top end side of a handle 95, it comes in contact with a spindle 26 through a second connector 113 instead of contacting the spindle 26 directly.

As shown in FIG. 21, concerning the ion toothbrush according to Embodiment 6, one electrode of the battery 14 is electrically connected with a terminal 18B of an LED 18 by means of a first connector 111. As in the aforementioned embodiments, this first connector 111 is also securely in contact with the battery 14 by means of its elasticity.

The terminal 18A of the LED 18 is electrically connected with a conductive slide spindle 112. This slide spindle 112 is composed of a round bar with a substantially circular cross section, and one end 112A thereof in contact with the end 18A of the LED 18 is bent in a substantially L shape. The slide spindle 112 has the sliding member 100 movably mounted thereon in the same manner as in Embodiment 5. On the top end side of a storage space 101, a spring 98 is placed.

The base end of the spindle 26 is electrically connected with a conductive second connector 113. This second connector 113 is composed of a round bar with a substantially circular cross section, and one end 113A thereof in contact with the base end of the spindle 26 is bent in a substantially L shape. The base end of the second connector 113 extends toward the base end side of the handle 95 so that the sliding member 100 can come in contact with the base end of the second connector 113 when the sliding member 100 moves toward the top end side of the handle 95.

Concerning the ion toothbrush having the above-described structure, when the sliding member 100 moves toward the top end side of the handle 95 along the slide spindle 112 by means of reciprocating motion of the handle 95, the sliding member 100 presses the spring 98 and can also come in contact with the base end of the second connector 113 exposed in the storage hole 101. The sliding member 100 contacting the second connector 113 is pushed back to the base end aide of the handle 95 by the urging force of the spring 98, thereby releasing the above-mentioned contact. At this time, if the handle 95 is moved in a reciprocating manner, this reciprocating motion also moves the sliding member 100 toward the base end side of the handle 95, thereby releasing the contact between the sliding member 100 and the second connector 113.

Embodiments 5 and 6 described cases where the sliding member 100 is used as a movable member. However, without limitation to such form of movable member, it is possible to use a rolling member 120 (such as a spheric member or a cylindrical member) made of a conductive material instead of the sliding member 100. Specifically speaking, the terminal 18A of the LED 18 and the base end of the spindle 26 are placed with a space between them at a rolling part 121, and when the rolling member 120 passes over the terminal 18A and the spindle 26 located at the rolling part 121 and the rolling member 120 then contacts the terminal 18A and the spindle 26, the LED 18 is caused to go on.

Examples of other forms of use of the sliding member 100 are shown in FIGS. 23 through 26. FIGS. 23 through 26 are schematic illustrations of the aforementioned electric circuit.

Figure 23:
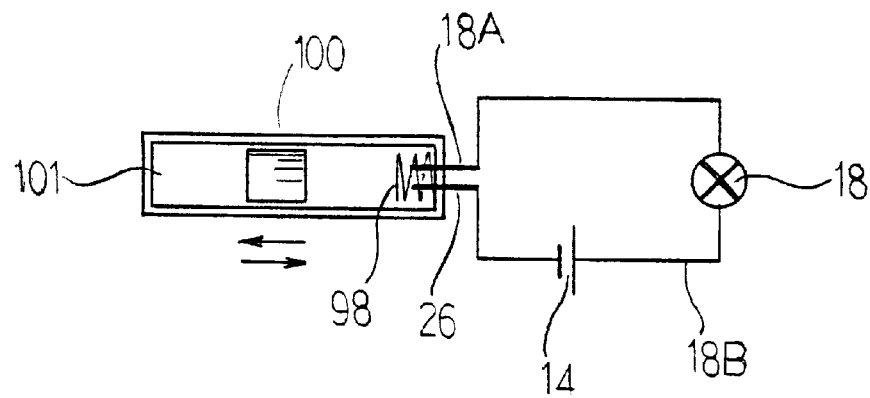
FIG. 23 is a schematic diagram of an electric circuit according to still another embodiment of this invention.

FIG. 23 illustrates an example where the terminal 18A of the LED 18 and the base end of the spindle 26 are exposed with a space between them in the storage hole 101 for receiving the sliding member 100, and when the sliding member 100 moves with the reciprocating motion of the handle 95 and then contacts the terminal 18A and the base end of the spindle 26, the LED 18 is caused to go on. Moreover, the spring 98 is located in the vicinity of the terminal 18A and the base and of the spindle 26, so that when the sliding member 100 contacts the terminal 18A and the spindle 26, the sliding member 100 is pushed back by the urging force of the spring 98, thereby opening the electric circuit. If the sliding member 100 collides with, not contacts, the terminal 18A and the spindle 26, the sliding member 100 will be bounced back by reaction force from the spindle 26 and the terminal 18A. The spring 98 prevents the electric circuit from being left closed when the toothbrush is placed at rest.

Figure 24:
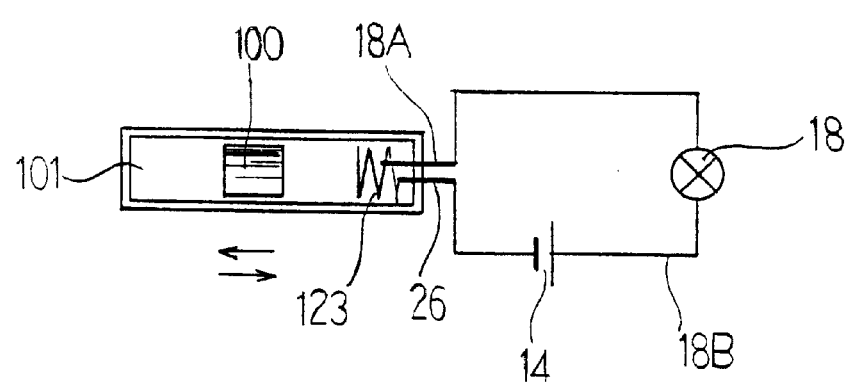
FIG. 24 is a schematic diagram of an electric circuit according to a further embodiment of this invention.

FIG. 24 illustrates an example where instead of the spring 98 in FIG. 23, the base end,of the spindle 26 is made into a spring 123. Other features are similar to those shown in FIG. 23.

Figure 25:
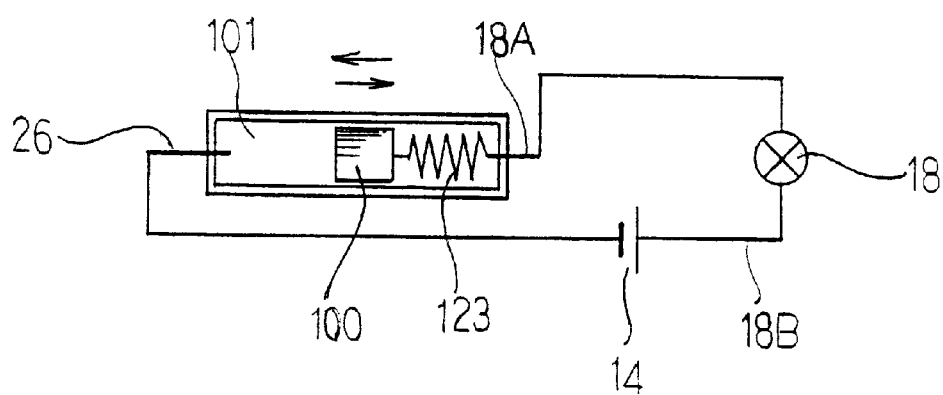
FIG. 25 is a schematic diagram of an electric circuit according to a still further embodiment of this invention.

FIG. 25 illustrates an example where the top end of the terminal 18A of the LED 18 is made into the spring 123, and the sliding member 100 is located at the top end of the spring 123. This ion toothbrush causes the sliding member 100 to move mainly with the reciprocating motion of the handle 95, thereby establishing or releasing the contact between the sliding member 100 and the spindle 26. The principal role of the spring 123 is to prevent the sliding member 100 from being left in contact with the spindle 26 when the toothbrush is not used and is placed at rest.

Figure 26:
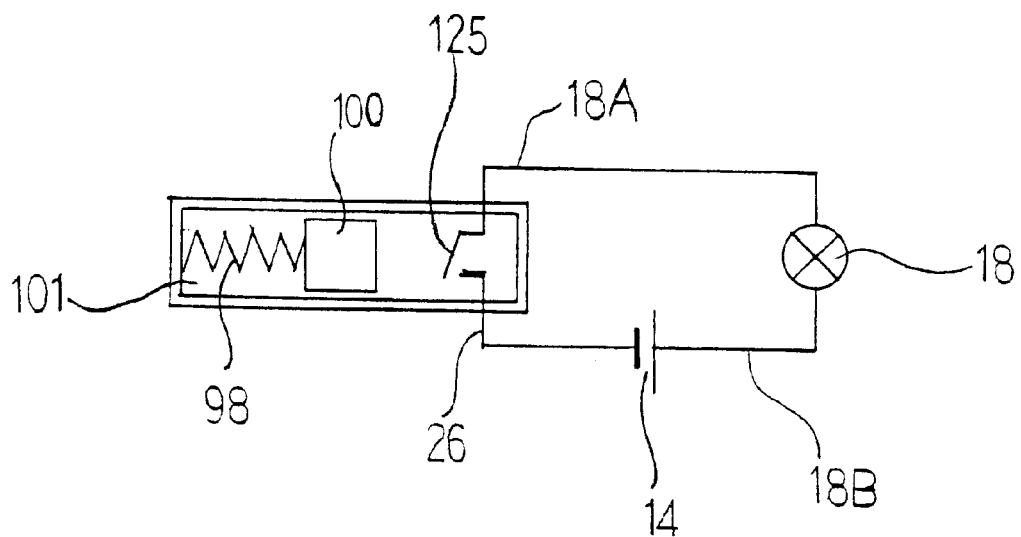
FIG. 26 is a schematic diagram of an electric circuit according to a yet further embodiment of this invention.

FIG. 26 illustrates an example where a switch part 125 is provided between the terminal 18A of the LED 18 and the base end of the spindle 26, and the sliding member 100 made of a non-conductive material is provided, which is supported by the spring 98 on the top end side of the storage hole 101. With this ion toothbrush, when the reciprocating motion of the handle 95 causes the sliding member 100 to move and the sliding member 100 then presses the switch part 125, the above-mentioned electric circuit is closed, thereby causing the LED 18 to go on. When the toothbrush is placed still with the spring 98 side up and the sliding member 100 side down, the role of the spring 98 is to, for example, prevent the sliding member 100 from pressing the switch part 125 with gravity to close the electric circuit.

Figure 27:
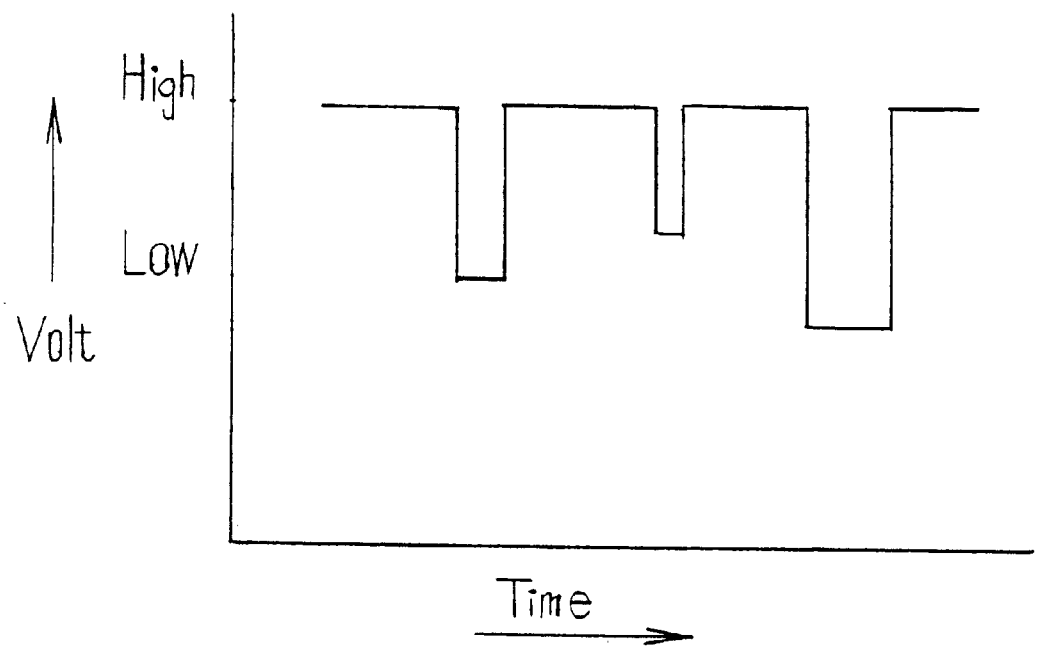
FIG. 27 is a diagram showing the relationship between voltage and time with regard to the electric circuit of the yet further embodiment of this invention.

When the LED 18 goes on, the voltage of electrons and the amount of an electric current passing from the spindle 26 and through the brush bristles 51 into the user's mouth are reduced. On the other hand, when the LED 18 goes off, the voltage of the electrons and the amount of the electric current return to the original state (ref. FIG. 27). Accordingly, brushing teeth in the reciprocating motion causes random flashing from once to several times per second, which results in a fluctuating low frequency current.

According to "Electronic Treatment Dictionary (*densbi chiryou daijiten*)" edited by Yasusaburo sugi, an emeritus professor at University of Tsukuba, it has been recently found through the studies of doctors around the world that particular actions caused by changes in the waveform or frequency of a low frequency current, rather than the positive or negative polarity, exert greater influence on the human body in practical applications. Specifically speaking, such changes in the waveform or frequency of the electric current promote the secretion of a natural analgesic substance called "endorphin" from a brainstem and also influence the working of a gate (barrier) for controlling dull pain, which is located at the spinal cord.

When a low frequency current is fed from above the skin, this stimulus gives normal excitement to nerves, thereby recovering the natural proper working. Therefore, the general low frequency treatment is called "TENS (Transcutaneous Electrical Nerve Stimulation)" in foreign countries.

Principal physiological effects of the low frequency treatment are as follows:

1. Effects on the Motor Nerve and Muscles
A massage effect and an exercise effect will be obtained.
2. Effects on the Autonomic Nerve
Effects on various chronic disease can be expected.
3. Effects on the Sensory Nerve
An analgesic effect will be exerted.

Concerning the low frequency treatment equipment of the manual type, general principles of frequencies for domestic treatment are as follows:

For stimulus energization: minimum frequencies from 1 Hz to 20 Hz; and

For extremities energization: low frequencies from 1 Hz to 50 Hz, and medium frequencies from 60 Hz to 125 Hz.

In a case of alternating current potential treatment, the potential (voltage) changes momentarily and, therefore, a fluctuating electric field (fluctuating electromagnetic field) is generated. Through recent studies, many domestic and foreign scholars have confirmed that if a fluctuating electric field is caused to act on the human body, it expedites the healing of wounds and remarkably promotes the healing of fractures.

Some recent treatment equipment applies computers to create more complicated fluctuating electric fields, and expectations are rising for the utility of such equipment. This equipment is sometimes called "potential treatment equipment of a fluctuating potential type" as distinguished from conventional potential treatment equipment called a "fixed potential type."

The aforementioned "Electronic Treatment Dictionary" contains the above descriptions. Accordingly, the vibration switch type ion toothbrush of this invention gives more advantageous working effects on the teeth and body. As compared with the aforementioned literature, changes of the potential (voltage) and the electric current are caused by the collisions of the movable member. Consequently, the toothbrush of this invention has the structure which is impulsive, highly stimulating, and very simple as shown in FIG. 27, the toothbrush of this invention generates such a fuzzy and complicated fluctuating electric field by means of the user's unconscious reciprocating notion to activate cells, as can be favorably compared with a complicated fluctuating electric field of the above-mentioned computer application. Moreover, since the toothbrush of this invention operates at a low potential, it is very safe. Also, every person habitually uses a toothbrush more than once every day. Accordingly, the toothbrush of this invention represents great advances as compared with the conventional ion toothbrush of the fixed potential type.

Embodiment 7

An explanation is hereinafter given about an ion toothbrush according to Embodiment 7 of this invention with reference to the relevant drawings.

Figure 30:
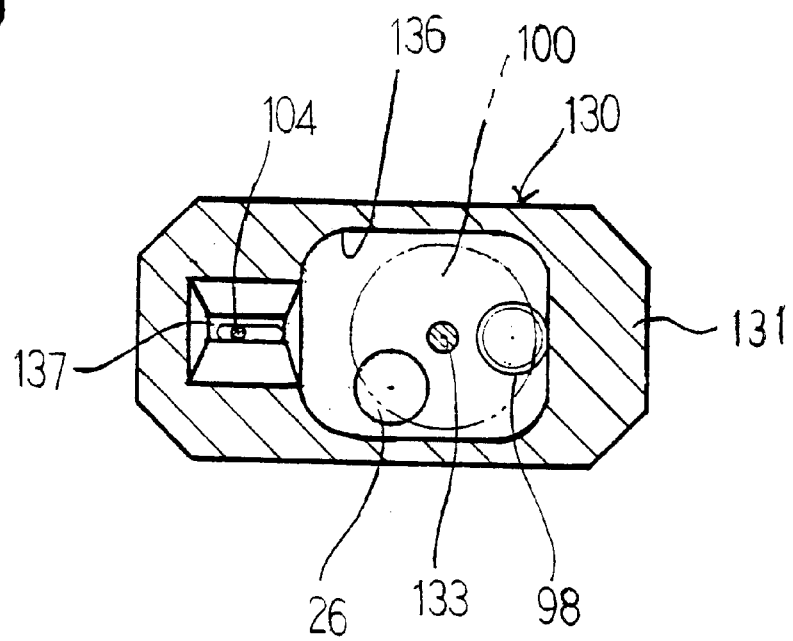
FIG. 30 is a cross section taken on line XXX—XXX in FIG. 28.
Figure 31:
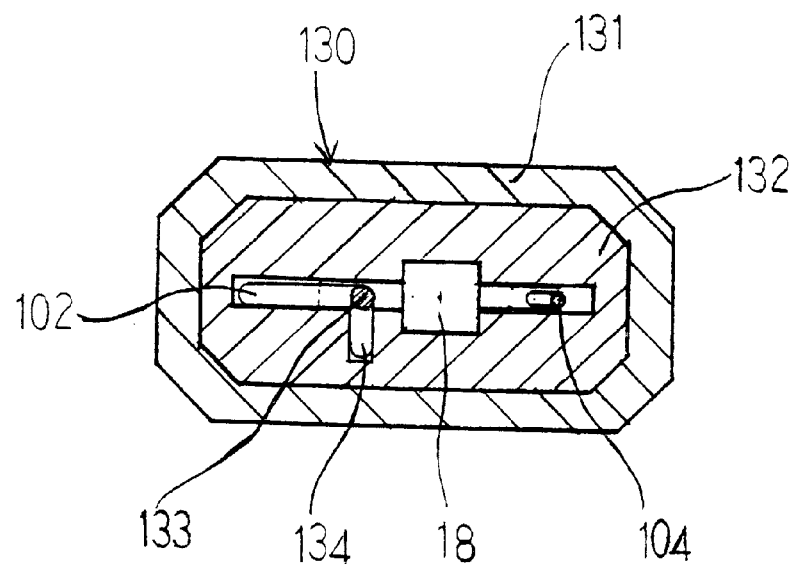
FIG. 31 is a cross section taken on line XXXI—XXXI in FIG. 28.
Figure 32:
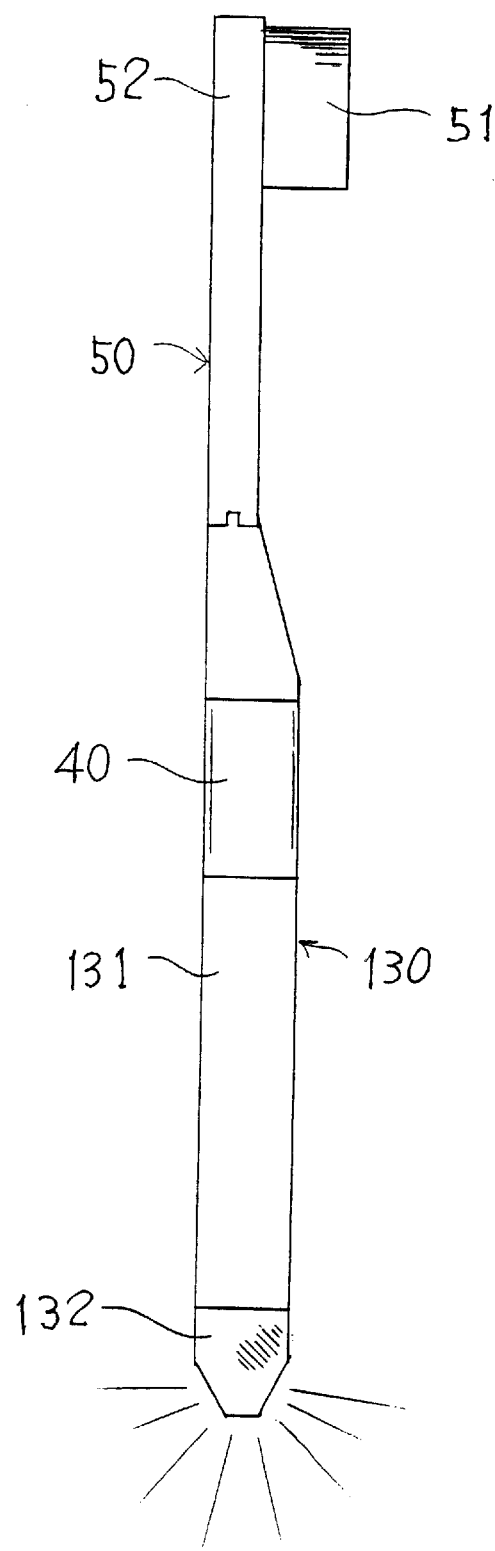
FIG. 32 is a side view of the ion toothbrush according to Embodiment 7.

FIG. 28 is a plan view of anion toothbrush according to Embodiment 7, which is partially sectioned on line XXVIII—XXVIII in FIG. 29. FIG. 29 is a cross section taken on line XXIX—XXIX in FIG. 28. FIG. 30 is a cross section taken on line XXX—XXX in FIG. 28, FIG. 31 is a cross section taken on line XXXI—XXXI in FIG. 28. FIG. 32 is a side view of the ion toothbrush according to Embodiment 7.

In Embodiment 7, members similar to those of the ion toothbrush according to Embodiment 5 are given the same reference numerals as in Embodiment 5, and any detailed description thereof is omitted.

The ion toothbrush according to Embodiment 7 is different from the ion toothbrush according to Embodiment 5 in that the base end side of a handle body is closed with a cap instead of closing the handle body with the cover, and also the shape of a slide spindle is different.

As shown in FIGS. 28 through 32, the ion toothbrush according to Embodiment 7 comprises: a handle 130 for a user to hold; and a head 50.

The handle 130 comprises: a handle body 131 for receiving parts as described later in detail; and a cap 132 which is provided on the base end side of the handle body 131 with the parts received therein, and which closes the handle body 131.

Inside of the handle body 131, the following holes are made: a storage hole 136 for receiving a spring 98, a part of a slide spindle 133, and a sliding member 100 as a movable member which is pierced in a manner movable relative to the slide spindle 133; and a storage hole 137 for receiving a part of a first connector 104.

The slide spindle 133 located in place of the slide spindle 99 as described in Embodiment 5 is formed with a conductive material and has a bend part 102 formed in a substantially C shape at its end on the base end side. Moreover, adjacent to the top end side of the bend part 102, there is a bend part 134 (as shown in FIG. 29) which is bent in a direction perpendicular to the bend part 102. The slide spindle 133 is secured in the up-and-down and right-and-left directions relative to the handle 130 by the bend parts 102 and 134. Moreover, the elasticity of the bend part 102 causes the base end of the slide spindle 133 to be securely electrically connected with the end 18A of the LED 18.

The cap 132 has a storage hole 135 for receiving the LED 18, the base end side of the slide spindle 133, which includes the bend parts 102 and 134, and the base end side of the first connector 104. The cap 132 is composed of a light transmittable material capable of transmitting light generated by the LED 18.

The ion toothbrush having the above-described structure can also easily test the supply voltage in the same manner as the ion toothbrush according to Embodiment 5 when a user shakes the ion toothbrush to move the handle 130 in a reciprocating mariner, which causes the sliding member 100 to move, thereby causing the flashing of the LED 18.

The user holds the handle with the brush bristles side up as a natural action and sees the flashing of the LED (illuminant) as he shakes the handle up and down.

At this time, if the spring 98 is located above the movable member 100, the amount of time when the electric circuit is closed under the action of gravity as the movable member 100 collides and contacts the spindle 26 of Embodiment 5 or the second connector 113 of Embodiment 6 is less than the case of Embodiment 7 where the spring 98 is located below the movable member 100. Accordingly, the LEDs 18 of Embodiments 5 and 6 are less brighter than the LED 18 of Embodiment 7.

Figure 33:
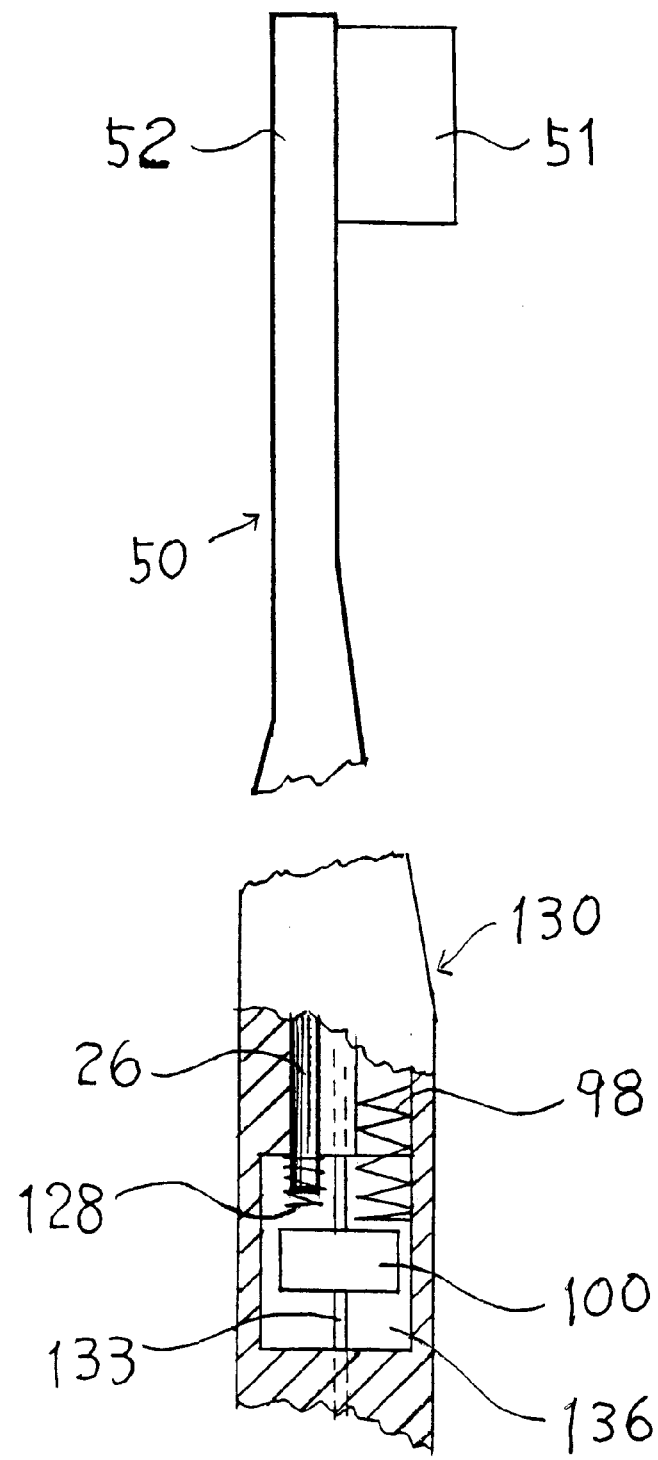
FIG. 33 is a schematic diagram of an electric circuit according to a yet further embodiment of this invention.

FIG. 33 illustrates an example where a spring 128 is provided at the end of the spindle 26 in order to maintain the light emitting time of the LED 18 for a long time. The ion toothbrush having such a structure can slow down the timing of the movable member 100 to fall down under the action of gravity, thereby making it possible to lengthen the time of contact between the spindle 26 and the movable member 100 through the spring 128 and to enhance the brightness of the LED 18.

Embodiment 8

An explanation is hereinafter given about an ion toothbrush according to Embodiment 8 of this invention with reference to the relevant drawings.

Figure 36:
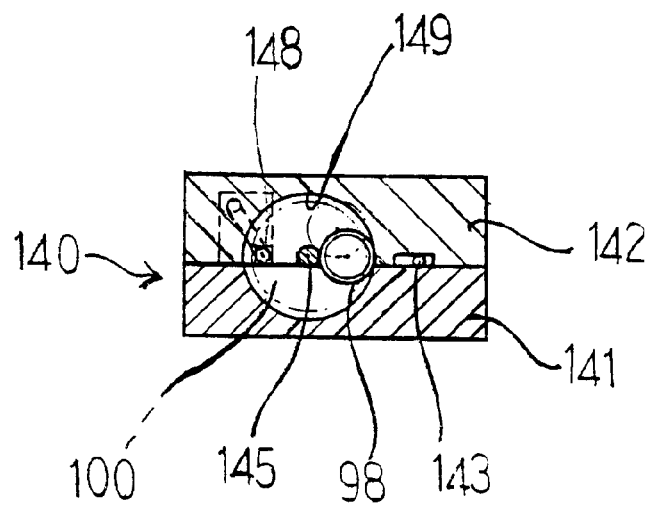
FIG. 36 is a cross section taken on line XXXVI—XXXVI in FIG. 34.
Figure 37:
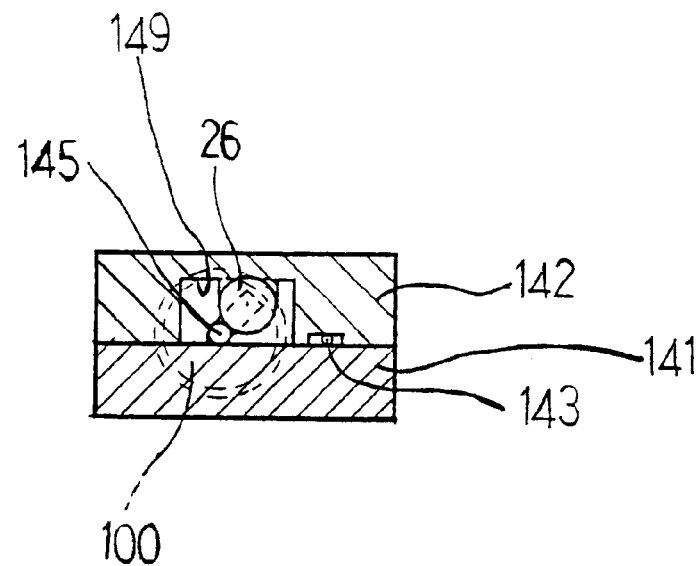
FIG. 37 is a cross section taken on line XXXVII—XXXVII in FIG. 34.

FIG. 34 is a plan view of an ion toothbrush according to Embodiment 8 with its cover removed therefrom. FIG. 35 is a side view of the ion toothbrush according to Embodiment 8. FIG. 36 is a cross section taken on line XXXVI—XXXVI in FIG. 34. FIG. 37 is a cross section taken on line XXXVII—XXXVII in FIG. 34.

In Embodiment 8, members similar to those described in the above-mentioned embodiments are given the same reference numerals as in the above-mentioned embodiments, and any detailed description thereof is omitted.

As shown in FIGS. 34 through 37, the ion toothbrush according to Embodiment 8 comprises: a handle 140 for a user to hold; and a head 50 (not shown in the drawings).

The handle 140 comprises: a handle body 141 for receiving parts as described later in detail; and a cover 142 which is provided on the handle body 141 with the parts received therein, and which closes the handle body 141.

Inside of the handle body 141, the following holes are made: a storage hole 144 for receiving a first connector 143, and a storage hole 147 for receiving a spring 98, a slide spindle 145, a sliding member 100 as a movable member which is pierced in a manner movable relative to the slide spindle 145, a third connector 146 capable of electrically connecting the movable member 100 with a terminal of an LED 18, and the LED 18.

A substantially center part of the first connector 143 forms a bend part 102 in a substantially C shape. As in the aforementioned embodiments, the elasticity of the bend part 102 and the elasticity of the first connector 143 itself causes one end of the first connector 143 to be secured to the battery 14 and also causes the other end of the first connector 143 to be secured to the terminal 18B of the LED 18 with certainty.

The top end of the slide spindle 145 is electrically connected with the spindle 26. This slide spindle 145 is formed with a conductive material and has a bend part 102 in a substantially C shape at a position close to its top end. In the same manner as described above, the top end of this slide spindle 145 is securely electrically connected with the spindle 26 by means of the elasticity of the bend part 102.

The third connector 146 has a bend part 148 in a substantially U shape at its substantially center position. One end of this third connector 146 is also securely electrically connected with the terminal 18A of the LED 18 by means of the elasticity of the bend part 148. The other end of the third connector 146 is placed at a position corresponding to the movable member 100, where the other end of the third connector 146 can contact the movable member 100 when the movable member 100 moves.

As specifically shown in FIGS. 36 and 37, the cover 142 has a storage hole 149 formed therein for receiving the respective parts placed in the handle body 141.

In Embodiment 8, at least one of the cover 142 and the handle body 141 is composed of a light transmittable material capable of transmitting light generated by the LED 18.

If the ion toothbrush having the above-described structure is placed with the brush bristles side up under normal conditions, the movable member 100 moves downward (toward the side of the third connector 148) under the action of gravity, but does not contact the third connector 148 because of the urging force of the spring 98. Accordingly, the LED 18 will not go on. When a user brushes his teeth and moves the handle in a reciprocating manner, the movable member 100 collides with and contacts the third connector 148 against the urging force of the spring 96, and a reaction force of the collision then releases the contact with the third connector 148 again. At this time, the urging force of the spring 98 also contributes to the release from the contact. Repetition of such motion causes the flashing of the LED 18.

The above-mentioned embodiments described an ion toothbrush which is structured to have its handle separable from its head. However, without limitation to such a structure, it is certain that the handle and the brush part of the ion toothbrush of this invention may be integrally formed.

Moreover, the above-mentioned embodiments described an ion toothbrush. However, without limitation of such type of toothbrush, it is obvious that the present application can be applied to any toothbrush that uses a battery for brushing teeth in order to test the effectiveness of the battery.

Furthermore the above-mentioned embodiments described the employment of an LED (illuminant) as an example of the means of indicating the effectiveness of the battery. However, without limitation to such means, a sounding member for producing sound may be used instead of the LED, or both the illuminant and the sounding member may be used.

INDUSTRIAL APPLICABILITY

With the toothbrush of this invention, it is possible to turn on and off the illuminant for testing the effectiveness of the battery by using a switch. Accordingly, in contrast to the structure with a plurality of electronic parts which always causes the emission of light and sound, it is possible to easily make the toothbrush of this invention widespread as a daily product.

Moreover, since the effectiveness of the battery can be tested by opening or closing the electric circuit including the illuminant, the conductive spindle, and the battery, it is possible to minimize the increase in the number of parts as necessary. Therefore, it is possible to provide a toothbrush with simplified assembling steps.

What is claimed is:
1. A ion toothbrush comprising:
   a head with brush bristles implanted therein;
   a handle for a user to hold; and
   a battery received in the handle,
     wherein one electrode of the battery is conductively connected with the external surface of the handle and the other electrode of the battery is conductively connected with the vicinity of the implanted area of the brush bristles at the head, and
   the ion toothbrush further comprising:
     an illuminate with its one terminal connected to one electrode of the battery and with its other terminal connected to the other electrode of the battery;
     a conductive spindle capable of conductively connecting the other electrode of the battery with the vicinity of the implanted area of the brush bristles and also capable of conductively connecting with the other terminal of the illuminant;
     a switch for opening and closing an electric circuit including the illuminant, the conductive spindle, and the battery;
     a first connector for electrically connecting one electrode of the battery with one terminal of the illuminant; and
     a second connector for electrically connecting the other electrode of the battery with the other terminal of the illuminant,
   wherein at least one of the first and second connectors electrically connects, because of its elasticity, with the battery, wherein one end of the first connector is secured to the handle and the other end of the first connector is urged by its elasticity toward one electrode of the battery.

2. An ion toothbrush according to claim 1, wherein the switch includes a switch knob, and pressing the switch knob closes the electric circuit.

3. An ion toothbrush according to claim 2, wherein as the switch knob is pressed, the switch causes the conductive spindle to conductively connect with the other terminal of the illuminant.

4. An ion toothbrush according to claim 2, wherein the handle comprises: a handle body with a parts storage space formed therein; and a closing cover for covering the parts storage space.

5. An ion toothbrush according to claim 4, wherein the switch knob is formed integrally with the closing cover.

6. An ion toothbrush according to claim 5, wherein the switch knob is composed of an elastic displacement member formed integrally with the closing cover.

7. An ion toothbrush according to claim 4, wherein the closing cover has a switch knob hole formed therein for fittingly setting the switch knob.

8. An ion toothbrush according to claim 4, wherein the closing cover has a battery hole formed therein, which can expose one electrode of the battery.

9. An ion toothbrush according to claim 2, wherein a light transmitting part capable of transmitting light generated by the illuminant is provided at least at a part of the switch knob.

10. An ion toothbrush according to claim 4, wherein the closing cover is made of a light transmittable material capable of transmitting light generated by the illuminant.

11. An ion toothbrush according to claim 4, wherein the parts storage space receives at least a part of the battery, the illuminant, both terminals of the illuminant, and the switch.

12. An ion toothbrush according to claim 11, wherein parts placed in the parts storage space are secured by closing the handle body with the-closing cover.

13. An ion toothbrush according to claim 4, wherein at least a part of the conductive spindle is exposed to the parts storage space.

14. An ion toothbrush according to claim 1, wherein the switch is located at a position somewhere between one electrode of the battery, one terminal of the illuminant, the illuminant, the other terminal of the illuminant, the conductive spindle, and the other electrode of the battery.

15. An ion toothbrush according to claim 1, wherein the first connector is composed of a round bar with a substantially circular cross section and with its one end bent to be placed in and secured to a first groove formed in the handle.

16. An ion toothbrush according to claim 1, wherein the second connector is urged by its elasticity toward the conductive spindle, thereby electrically connecting with the other electrode of the battery.

17. An ion toothbrush according to claim 1, wherein one end of the second connector is secured to the handle.

18. An ion toothbrush according to claim 17, wherein the second connector is composed of a round bar with a substantially circular cross section and with its one end bent to be placed in and secured to a second groove formed in the handle.

19. An ion toothbrush according to claim 1, wherein the first connector is electrically connected through a wiring board to one terminal of the illuminant, the second connector is electronically connected through the wiring board to the other terminal of the illuminant, and both terminals of the illuminant are electrically connected to the wiring board by means of an urging force of a conductive elastic member.

20. An ion toothbrush according to claim 19, wherein the handle comprises a handle body with a parts storage space formed therein, and a cover for closing the parts storage space, and the parts storage space receives at least the first and second connectors, the wiring board, the elastic member, and the illuminant, and the first and second connectors, the wiring board, the elastic member, and the illuminant are secured by closing the handle body with the cover.

21. An ion toothbrush according to claim 1, wherein the first connector is urged by its elasticity toward a conductive member electrically connected with one electrode of the battery, and the first connector thereby electrically connected with the one electrode.

\* \* \* \* \*